United States Patent
Zelik et al.

(10) Patent No.: US 12,138,785 B2
(45) Date of Patent: Nov. 12, 2024

(54) MOMENT ARM EXTENSION SYSTEM FOR EXOSUIT

(71) Applicant: Vanderbilt University, Nashville, TN (US)

(72) Inventors: Karl Zelik, Nashville, TN (US); Erik Lamers, Pittsburgh, PA (US); Keaton Scherpereel, Flagstaff, AZ (US)

(73) Assignee: Vanderbilt University, Nashville, TN (US)

( * ) Notice: Subject to any disclaimer, the term of this patent is extended or adjusted under 35 U.S.C. 154(b) by 311 days.

(21) Appl. No.: 17/615,053

(22) PCT Filed: May 28, 2020

(86) PCT No.: PCT/US2020/034999
§ 371 (c)(1),
(2) Date: Nov. 29, 2021

(87) PCT Pub. No.: WO2020/243366
PCT Pub. Date: Dec. 3, 2020

(65) Prior Publication Data
US 2022/0219313 A1    Jul. 14, 2022

Related U.S. Application Data

(60) Provisional application No. 62/853,422, filed on May 28, 2019.

(51) Int. Cl.
*B25J 9/00* (2006.01)
*A61H 1/02* (2006.01)
*B25J 9/10* (2006.01)

(52) U.S. Cl.
CPC .......... *B25J 9/0006* (2013.01); *A61H 1/0244* (2013.01); *A61H 1/0292* (2013.01);
(Continued)

(58) Field of Classification Search
CPC .... A61H 2003/0283; A61H 2201/1602; A61H 2201/1623; A61F 5/02; A61F 5/026;
(Continued)

(56) References Cited

U.S. PATENT DOCUMENTS 330,213 A    11/1885    Deweese
551,839 A    12/1895    Jw
(Continued)

FOREIGN PATENT DOCUMENTS

DE    10 2004 009 315 A1    9/2005
DE    202005011650 U1    12/2006
(Continued)

OTHER PUBLICATIONS

EP Extended Search Report issued in EP 20813296 dated Dec. 23, 2022.
(Continued)

*Primary Examiner* — Ophelia A Hawthorne
*Assistant Examiner* — Michael Milo
(74) *Attorney, Agent, or Firm* — Blank Rome LLP

(57) ABSTRACT

A moment arm extension system and method for improving the mechanical advantage of a wearable assistance device by increasing the moment arm of a force-bearing member relative to an underlying body segment of a user are disclosed. The moment arm extension system achieves this by shifting the force-bearing member to lie farther away from the body segment of the user.

18 Claims, 10 Drawing Sheets

(52) U.S. Cl.
CPC ....... *B25J 9/1045* (2013.01); *A61H 2201/165* (2013.01); *A61H 2201/5061* (2013.01)

(58) Field of Classification Search
CPC .... A61F 5/028; A61F 5/03; A61F 5/30; A61F 2005/0197; A61F 13/148; A61F 13/00038; F16D 13/58; A61B 5/389; A41C 1/08
USPC .......................................................... 601/33
See application file for complete search history.

(56) References Cited

U.S. PATENT DOCUMENTS

| | | | |
|---|---|---|---|
| 596,839 | A | 1/1898 | Bassett |
| 1,098,492 | A | 6/1914 | Gibson |
| 1,386,067 | A | 8/1921 | Mason |
| 1,553,874 | A | 9/1925 | Nivens |
| 4,709,692 | A | 12/1987 | Kirschenberg |
| 5,131,490 | A | 7/1992 | Bell |
| 5,256,135 | A | 10/1993 | Avihod |
| 5,709,648 | A | 1/1998 | Webb |
| 5,716,307 | A | 2/1998 | Vadher |
| 5,743,866 | A | 4/1998 | Bauerfeind et al. |
| 5,816,251 | A | 10/1998 | Glisan |
| 6,129,691 | A | 10/2000 | Ruppert |
| 6,190,342 | B1 | 2/2001 | Taylor |
| 6,450,131 | B1 | 9/2002 | Broman |
| 7,553,266 | B2 | 6/2009 | Abdoli-Eramaki |
| 8,241,090 | B2 | 8/2012 | Michael |
| 8,568,344 | B2 | 10/2013 | Ferguson |
| 8,832,863 | B2 | 9/2014 | Yang |
| 8,834,394 | B2 | 9/2014 | Ghajar |
| 9,682,005 | B2 | 6/2017 | Herr |
| 9,744,066 | B2 | 8/2017 | Kazerooni |
| 10,166,679 | B2 | 1/2019 | Tanibayashi |
| 10,463,562 | B2 | 11/2019 | Chavarria |
| 10,588,771 | B2 | 3/2020 | Holscher et al. |
| 2005/0130815 | A1* | 6/2005 | Abdoli-Eramaki ..... A61F 5/026 482/121 |
| 2005/0263990 | A1 | 12/2005 | Clute |
| 2007/0045570 | A1 | 1/2007 | Afanasenko et al. |
| 2009/0118655 | A1 | 5/2009 | Wang |
| 2010/0125230 | A1 | 5/2010 | Hurley |
| 2010/0204630 | A1 | 8/2010 | Sandifer et al. |
| 2012/0048904 | A1 | 3/2012 | Scicluna |
| 2012/0130293 | A1 | 5/2012 | Brown |
| 2012/0184881 | A1 | 7/2012 | Kobayashi et al. |
| 2013/0006386 | A1 | 1/2013 | Hansen |
| 2013/0160189 | A1 | 6/2013 | Yang |
| 2013/0211295 | A1 | 8/2013 | Johnson et al. |
| 2013/0296746 | A1 | 11/2013 | Herr |
| 2014/0100501 | A1 | 4/2014 | Burke et al. |
| 2014/0135674 | A1 | 5/2014 | Kirk |
| 2014/0277739 | A1 | 9/2014 | Kornbluh |
| 2015/0133842 | A1 | 5/2015 | Ferrigolo |
| 2015/0359698 | A1 | 12/2015 | Popovic et al. |
| 2016/0107309 | A1 | 4/2016 | Walsh et al. |
| 2016/0193067 | A1 | 7/2016 | Petursson et al. |
| 2016/0220438 | A1* | 8/2016 | Walsh ........................ A61F 2/68 |
| 2016/0250062 | A1 | 9/2016 | Radaelli |
| 2017/0165088 | A1 | 6/2017 | Lefeber |
| 2017/0209330 | A1 | 7/2017 | Hughes et al. |
| 2017/0232617 | A1 | 8/2017 | Tanibayashi et al. |
| 2018/0093374 | A1 | 4/2018 | Holgate |
| 2018/0193686 | A1 | 7/2018 | Adeeko, Jr. |
| 2018/0221189 | A1 | 8/2018 | Garth et al. |
| 2019/0015235 | A1 | 1/2019 | Badger |
| 2019/0231574 | A1 | 8/2019 | Kazerooni |
| 2019/0358074 | A1 | 11/2019 | Zelik et al. |
| 2019/0380904 | A1 | 12/2019 | Panizzolo et al. |
| 2020/0038219 | A1 | 2/2020 | Mizera et al. |

FOREIGN PATENT DOCUMENTS

| | | |
|---|---|---|
| DE | 102015208125 A1 | 11/2016 |
| JP | 2008/067762 A | 3/2008 |
| JP | 2013 144858 A | 7/2013 |
| JP | 2016 083254 A | 5/2016 |
| KR | 1020160031603 | 3/2016 |
| KR | 20170005173 A | 1/2017 |
| WO | WO 2005/056124 A1 | 6/2005 |
| WO | WO 2018/122100 A1 | 7/2010 |
| WO | WO 2015/088863 A2 | 6/2015 |
| WO | WO 2015/157731 A1 | 10/2015 |
| WO | 2017173441 A1 | 10/2017 |
| WO | WO 2018/067363 A1 | 4/2018 |
| WO | 2018122106 A1 | 7/2018 |
| WO | WO 2018/136722 A1 | 7/2018 |
| WO | WO 2019/161232 A1 | 8/2019 |

OTHER PUBLICATIONS

International Search Report and Written Opinion from PCT/US2021/022531 dated Jun. 3, 2021.
Yumeko Imamura et al: "Motion-based design of elastic belts for passive assistive device using musculoskeletal model", Robotics and Biomimetics (ROBIO), 2011 IEEE International Conference On, IEEE, Dec. 7, 2011 (Dec. 7, 2011), pp. 1343-1348, XP032165973, DOI: 10.1109/ROBIO.2011.6181475 ISBN: 978-1-4577-2136-6.
Communication pursuant to Article 94(3) EPC dated Jul. 8, 2022 from corresponding EP Application No. 18 741 272.1.
Extended European Search Report mailed Jun. 1, 2023, issued in counterpart EP application No. 20814224.0.
Written Opinion of the International Searching Authority for International Application No. PCT/US2018/014393 dated May 17, 2018.
International Search Report for International Application No. PCT/US2018/014393, mailed May 12, 2018.
International Preliminary Report on Patentability for International Application No. PCT/US2018/014393, dated Jul. 23, 2019.
ISB Poster Final EPL, (Create) Mar. 2016 (Mar. 2016); retrieved from the internet Apr. 19, 2019; https://s3.amazonaws.com/vu-my/wp-content/uploads/sites/1409/2016/03/31171620/ISB-Poster-Final-EPL.pdf., "How It's Controlled," Middle Figure and Assistive Garment Prototype Figure.
International Search Report of International Application No. PCT/US21/37579.
Nasiri et al., "Reducing the Energy Cost of Human Running Using an Unpowered Exoskeleton", IEEE Transactions on Neural Systems and Rehabilitation Engineering, vol. 26, No. 10, Oct. 2018, pp. 2026-2032.
Simpson et al., "Connecting the legs with a spring improves human running economy", Journal of Experimental Biology, 2019, pp. 1-10.
Chaichaowarat et al., "Passive Knee Exoskeleton Using Torsion Spring for Cycling Assistance", IEEE, 2017, pp. 3069-3074.
Ranaweera et al., "Development of A Passively Powered Knee Exoskeleton for Squat Lifting", Journal of Robotics, Networking and Artificial Life, vol. 5, No. 1, 2018, pp. 45-51.
Rogers et al., "A Quasi-Passive Knee Exoskeleton to Assist During Descent", 2017, pp. 63-67.
Sridar et al., "Development of a Soft Inflatable Exosuit for Knee Rehabilitation", 2017 IEEE/RSJ (IROS), pp. 3722-3727.
Elliott et al., "Design of a Clutch-Spring Knee Exoskeleton for Running", Journal of Medical Devices, 2014, vol. 8, pp. 1-11.
Lamers, "Modeling, Design and Evaluation of a New Extensible Moment Arm Mechanism to Improve Exosuit Comfort and Performance", pp. 1-21.
International Search Report and Written Opinion, mail date Nov. 28, 2023, 19 pages, received in corresponding PCT application No. PCT/2023/US066231.
European Search Report received in corresponding patent application No. 21772646.2, issued Mar. 19, 2024.
1 Extended European Search Report mailed Jun. 1, 2023, issued in counterpart EP application No. 20814224.0.

(56) References Cited

OTHER PUBLICATIONS

Lamers, Erik P. et al., "Feasibility of a Biomechanically-Assistive Garment to Reduce Low Back Loading During Leaning and Lifting", CREATE, (Sep. 14, 2016), URL: https://s3.amazonaws.com/vu-my/wp-content/uploads/sites/1409/2016/03/31171620/ISB-Poster-Final-EPL.pdf, (Apr. 19, 2018), XP055514236.
Partial Supplementary European Search Report issued in App. No. EP21825853, dated Jun. 14, 2024, 14 pages.
Office Action dated Sep. 6, 2024 for U.S. Appl. No. 17/615,062 (pp. 1-39).

* cited by examiner

MOMENT ARM EXTENSION SYSTEM FOR EXOSUIT

CROSS REFERENCE TO RELATED APPLICATION(S)

This application is a U.S. National Stage Application of International Application No. PCT/US2020/034999, filed on May 28, 2020, which claims priority to U.S. Provisional Application No. 62/853,422, filed on May 28, 2019, both of which are hereby incorporated herein by reference in their entirety.

FIELD OF THE INVENTION

Embodiments are in the field of wearable assistance devices such as exosuits/exoskeletons. More particularly, embodiments disclosed herein relate to moment arm extension systems and methods for improving the mechanical advantage of wearable assistance devices by increasing the moment arm of a force-bearing member relative to an underlying body segment (e.g., a body joint) of a user.

BACKGROUND OF THE INVENTION

In recent years, there has been rapid growth in the development of occupational exoskeletons and exosuits, and these technologies are being adopted for various industrial applications. Despite the promising trajectory of these devices, a number of factors have limited their rate of adoption. Critical among these limiting factors are comfort and form-factor. Users are unlikely to adopt a wearable device if it is uncomfortable or if it protrudes out from their body in a way that is obstructive, unsafe or restricts movements needed to do their job.

The comfort of a wearable device is affected by the location, magnitude, direction and duration of force it applies to the body (device-to-body forces). These device-to-body forces are crucial because they create the assistive torque about a body segment of interest. However, the location, orientation and magnitude of these device-to-body forces can be altered while providing the same assistance (e.g., lumbar extension torque) to the user. For example, rigid exoskeletons typically use components to apply device-to-body forces mostly perpendicular to the length of the body segments to create torque. Whereas soft exosuits generally use textiles (and other soft-goods) to apply device-to-body forces oriented largely in parallel with the body segments.

Each design approach (rigid exoskeleton and soft exosuit) has benefits and drawbacks. Rigid exoskeletons, for example, often have larger moment arms than exosuits (by nature of applying perpendicular device-to-body forces farther away from the biological joint center-of-rotation), but the rigid components of exoskeletons also tend to be heavy, create pressure-points, discomfort and/or movement interference. Exosuits can be made of mostly soft and flexible materials which tend to be light-weight, minimize pressure points, movement interference and associated discomfort, but exosuit moment arms are generally smaller (limited by user morphology). There may be ways to hybridize these design approaches, by blending form-factor benefits of soft exosuits with the mechanical advantage afforded by larger moment arms of rigid exoskeletons.

Thus, it is desirable to provide a system and method for improving the mechanical advantage of a wearable assistance device by increasing the moment arm of a force-bearing member relative to an underlying body segment of a user to overcome the above disadvantages.

Advantages of the present invention will become more fully apparent from the detailed description of the invention hereinbelow.

SUMMARY OF THE INVENTION

Embodiments are directed to a wearable assistance device configured to be worn by a user. The device comprises: an upper body interface; a lower body interface; a moment arm extension system configured to be positioned along a body segment of the user, and be movable between a collapsed configuration and an extended configuration; and one or more elastic members operatively coupling the upper body interface to the lower body interface via the moment arm extension system. The moment arm extension system is operatively connected to at least one of the one or more elastic members at a location between the upper body interface and the lower body interface. The moment arm extension system allows a portion of the at least one of the one or more elastic members to extend away from the body segment when in the extended configuration, and to move towards the body segment when moving from the extended configuration to the collapsed configuration. The portion of the at least one of the one or more elastic members is further from the body segment when in the extended configuration than when in the collapsed configuration, such that the moment arm extension system provides a greater mechanical advantage (e.g., assistive torque or assistive moment of force) by the one or more elastic members about the body segment or another body segment when in the extended configuration than provided by the moment arm extension system when in the collapsed configuration.

Embodiments are also directed to a moment arm extension system configured to be worn by a user. The system comprises: a base configured to be positioned along a body segment of the user; and an extendable member operatively connected to the base. The moment arm extension system is movable between a collapsed configuration and an extended configuration. At least a portion of the extendable member extends a greater distance from the base when in the extendable configuration than in the collapsed configuration. The moment arm extension system is configured to operatively connect to at least one elastic member via the extendable member. The moment arm extension system allows a portion of the at least one elastic member to extend away from the body segment via the extendable member when in the extended configuration, and to move towards the body segment when moving from the extended configuration to the collapsed configuration. The portion of the at least one elastic member is further from the body segment when in the extended configuration than when in the collapsed configuration, such that the moment arm extension system provides a greater mechanical advantage by the at least one elastic member about the body segment or another body segment when in the extended configuration than provided by the moment arm extension system when in the collapsed configuration.

Embodiments are further directed to a moment arm extension system configured to be worn by a user. The system comprises: a flexible member having an upper portion and configured to be positioned along a body segment of the user. The flexible member is movable between a collapsed configuration and an extended configuration. A portion of the flexible member extends a greater distance from the body segment when in the extendable configuration than in the collapsed configuration. The flexible member is configured to allow a portion of an elastic member to extend away from the body segment via the portion of the flexible member when in the extended configuration, and to move towards the body segment when moving from the extended configuration to the collapsed configuration. The portion of the elastic member is further from the body segment when in the extended configuration than when in the collapsed configuration, such that the flexible member provides a greater mechanical advantage by the elastic member about the body segment or another body segment when in the extended configuration than provided by the flexible member when in the collapsed configuration.

Embodiments are yet further directed to a method of using a wearable assistance device. The method comprises providing a wearable assistance device to be worn by a user. The wearable assistance device comprises: an upper body interface; a lower body interface; a moment arm extension system positioned along a body segment of the user, and movable between a collapsed configuration and an extended configuration; and one or more elastic members operatively coupling the upper body interface to the lower body interface via the moment arm extension system, wherein the moment arm extension system is operatively connected to at least one of the one or more elastic members at a location between the upper body interface and the lower body interface. The method also comprises extending, via the moment arm extension system, a portion of the at least one of the one or more elastic members away from the body segment when in the extended configuration. The method further comprises moving, via the moment arm extension system, the portion of the at least one of the one or more elastic members towards the body segment when moving from the extended configuration to the collapsed configuration. The portion of the at least one of the one or more elastic members is further from the body segment when in the extended configuration than when in the collapsed configuration, such that the moment arm extension system provides a greater mechanical advantage by the one or more elastic members about the body segment or another body segment when in the extended configuration than provided by the moment arm extension system when in the collapsed configuration.

Additional embodiments and additional features of embodiments for the wearable assistance device, moment arm extension system, and method of using a wearable assistance device including a moment arm extension system are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the figures. The detailed description will refer to the following drawings in which like numerals, where present, refer to like items.

FIG. 16A shows a knee-assist exosuit, FIG. 16B shows a neck-assist exosuit, and FIG. 16C shows a bicep-assist exosuit.

DETAILED DESCRIPTION OF THE INVENTION

Figure 1A:
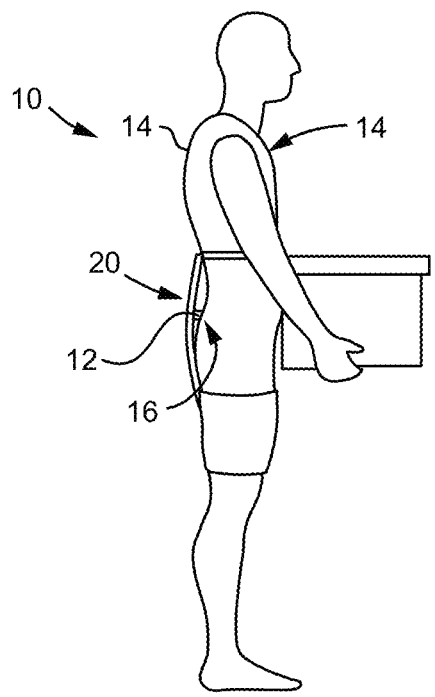
FIGS. 1A-1B are schematic diagrams illustrating an exosuit worn by a user and having a moment arm extension system of a hinge-lever design placed on the user's lumbar spine between the harness and thigh sleeve portions of the exosuit, in a collapsed configuration and extended configuration, respectively.

It is to be understood that the figures and descriptions of the present invention may have been simplified to illustrate elements that are relevant for a clear understanding of the present invention, while eliminating, for purposes of clarity, other elements found in a typical wearable assistance device or typical method of using a wearable assistance device. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

For purposes of this disclosure, the phrase "body segment" may include a body part such as a back, lumbar spine, hip, neck, etc., or a body joint such as an ankle, knee, elbow, wrist, etc., and thus, may all be used interchangeably. Also, the phrase "body segment" may include multiple body parts or body joints.

For purposes of this disclosure, the phrases "collapsed configuration" and "disengaged configuration" may be used interchangeably.

For purposes of this disclosure, the phrases "extended configuration" and "engaged configuration" may be used interchangeably.

For purposes of this disclosure, the phrase "mechanical advantage" may include "assistive torque" or "assistive moment of force", and thus, may all be used interchangeably.

For purposes of this disclosure, the phrase "wearable assistance device" may be an exosuit, exoskeleton, or other device that provides mechanical advantage about a body segment of a user.

For purposes of this disclosure, the phrase "elastic member" may be any member that has an amount of elasticity associated with it and which can take the form of, for example, a spring, cable, string, strap, cord, webbing, rope, band, gas-spring, pneumatic, etc., and may be coiled or non-coiled.

For purposes of this disclosure, the phrases "upper body interface" and "lower body interface" refer to body interfaces that can be positioned anywhere on the user's body, with the upper body interface placed higher relative to the lower body interface, assuming the user is in a standing/vertical position.

Embodiments of this disclosure reduce device-to-body forces of a exosuit (e.g., of low-back type) using an extensible moment arm extension system in order to improve wearer comfort and/or enhance device performance (i.e., level of assistance provided). Alternatively, for a fixed amount of force going through an elastic member, the embodiments of this disclosure increased the mechanical advantage provided about a body segment. A biomechanical model of the exosuit-human system is described below. Insights from this model are then employed in designing a novel low-back exosuit prototype that incorporates an extensible moment arm, followed by a human-subject case-study test for validation.

In previous work by the inventors, it has been shown that a low-profile exosuit, which can be worn underneath clothing, can reduce low-back muscle activity during lifting and bending tasks, and reduce the rate of muscle fatigue, by applying an assistive torque across the low-back. In brief, the inventors' previous exosuit described herein couples the wearer's trunk and thigh with an elastic band, so that when the user leans forward (via lumbar and/or hip flexion), the elastic band stretches, applying a force parallel to the lumbar extensor muscles (e.g erector spinae), and generating an assistive extension torque about the hip and spine. In updated exosuit designs, the inventors integrated a mode-switching clutch (both passive and powered versions), which allow the wearer to engage and disengage the exosuit assistance with the touch of a button. When engaged, the trunk and thigh are coupled with a stiff elastic band (i.e., strong enough to provide an assistive torque and offload the back muscles as it stretches). When disengaged, the trunk and thigh are coupled with a weak elastic band (providing minimal resistance and thus making the exosuit effectively transparent to the user as they move).

The previous exosuit was designed to fit close on the body and therefore has a relatively short moment arm (i.e., about 0.08 m from the L5S1 joint to the skin surface). To provide an assistive torque (e.g., 25 Nm about the L5S1) with this previous exosuit design, around 315 N is required of device-to-body forces on the shoulders. Although this is far below the average device-to-body discomfort limit, there are two relevant use-cases to consider. First, there may be individuals who are particularly sensitive to shoulder or thigh forces (e.g., due to a pre-existing condition) and for whom would want to achieve the same 25 Nm assistive torque, but with reduced device-to-body forces to ensure comfort. Second, there may be individuals who are perfectly comfortable with the nominal device-to-body forces, but who are engaged in heavy lifting, and would like to, for instance, double the magnitude of exosuit assistance (to 50 Nm) but while retaining the same comfortable magnitude of device-to-body forces on the shoulders and thighs.

One simple solution is to change the direction of the elastic band acting about the spine by adding a spacer behind the back. However, this solution introduces a new problem: the device now protrudes out from the back in a way that can interfere with movement, the environment and or other necessary tasks like sitting. The inventors investigated whether it was possible to boost the exosuit's mechanical advantage during lifting and bending, but without paying the interference penalty during other tasks.

Therefore, a goal of this work was to design, build and demonstrate feasibility of a novel type of exosuit that retains the low-profile form factor of the inventors' prior exosuit (e.g., for tasks like walking and sitting), and also retains the same magnitude of assistive torque (e.g., during lifting and/or leaning), but with lower device-to-body forces (i.e., for applications discussed above related to user comfort and heavy lifting). The inventors hypothesized that a moment arm extension system, which extends away from the back only when the exosuit is being used for assistance (i.e., is engaged, for example during lifting or leaning, see FIG. 1B), would reduce the device-to-body forces while providing the same magnitude of assistive torque (as an exosuit without the moment arm extension system). The implicit assumption here, which is based on the inventors' own experiences and observations, is that in most situations when a person is bending down to lift an object or is leaning forward (e.g., to reach for something) there is not another person/object mounting or encroaching on their backside. Thus, for most situations and occupations, the inventors would not expect this temporary protrusion from the body to interfere with the task or surrounding environment. Furthermore, because the moment arm extension system can collapse (and because the mode-switching exosuit can disengage the assistive force) and sit closely on the body, the exosuit can remain clothing-like, low-profile and unobtrusive during other activities (see FIG. 1A).

Figure 1B:
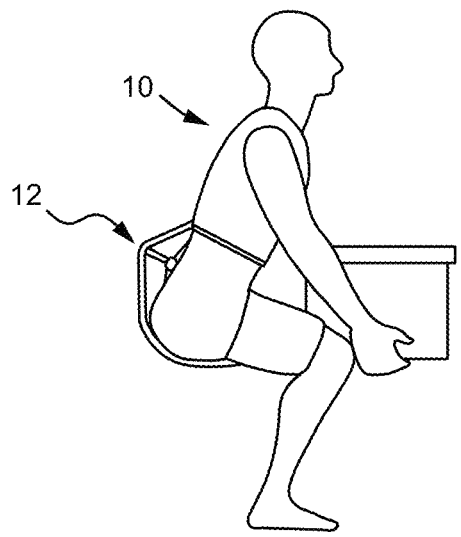

FIGS. 1A-1B are schematic diagrams illustrating an exosuit 10 worn by a user and having a moment arm extension system 12 of a hinge-lever design placed on the user's lumbar spine between the harness 14 and thigh sleeve portions 16 of the exosuit 10, in a collapsed configuration and extended configuration, respectively. In particular, FIGS. 1A-1B illustrates an exosuit with a moment arm extension system 12. The novel exosuit is composed of thigh interface 16 and trunk interface 14 which are coupled to each other by at least one elastic member 20. When the elastic member 20 encounters a force above a threshold (e.g., during lifting and/or leaning), the moment arm extension system 12 moves from a collapsed configuration (as shown in FIG. 1A) to an extended configuration (as shown in FIG. 1B). In the extended configuration, a lever 22 (FIG. 7B) of the moment arm extension system 12 is passively extended, thus increasing the effective moment arm of the exosuit 10 in relation to the L5S1 joint.

In an alternative embodiment, an optional clutch (powered or passive) may be employed to adjust the tension force of the one or more elastic members 20 coupling the thigh and trunk interfaces 16 and 14, or to adjust how this force is applied to the moment arm extension system 12.

In summary, this novel exosuit blends the beneficial aspects of rigid exoskeletons (i.e., having larger moment arms) and soft exosuits (i.e., having an unrestrictive and comfortable form-factor) by using a moment arm extension system to temporarily increase the exosuit moment arm when it is engaged to assist.

The inventors approach involved a sequence of biomechanical modeling followed by user-centered iterative mechanical design, after which a prototype was fabricated and feasibility was demonstrated in a human subject case study. The biomechanical modeling was necessary because there are a number of exosuit design parameters that can be manipulated, and it was initially unknown which of these parameters were most important to reduce device-to-body forces, how these parameters interact, or how to select these parameters to achieve the design goals. A biomechanical exosuit-human model was therefore developed to gain insight and inform selection of exosuit design parameters. Next, an exosuit prototype was designed and fabricated based on the model insights and then a human-subject case-study was performed. A case-study goal was to confirm that the novel exosuit prototype: (i) reduced device-to-body forces when it was engaged and provided the same magnitude of torque assistance as the inventors' previous exosuit (i.e., without the moment arm); and (ii) remained low-profile when it was disengaged (e.g., such that user could still, for example, sit down in a chair without interference from the exosuit).

Figure 2:
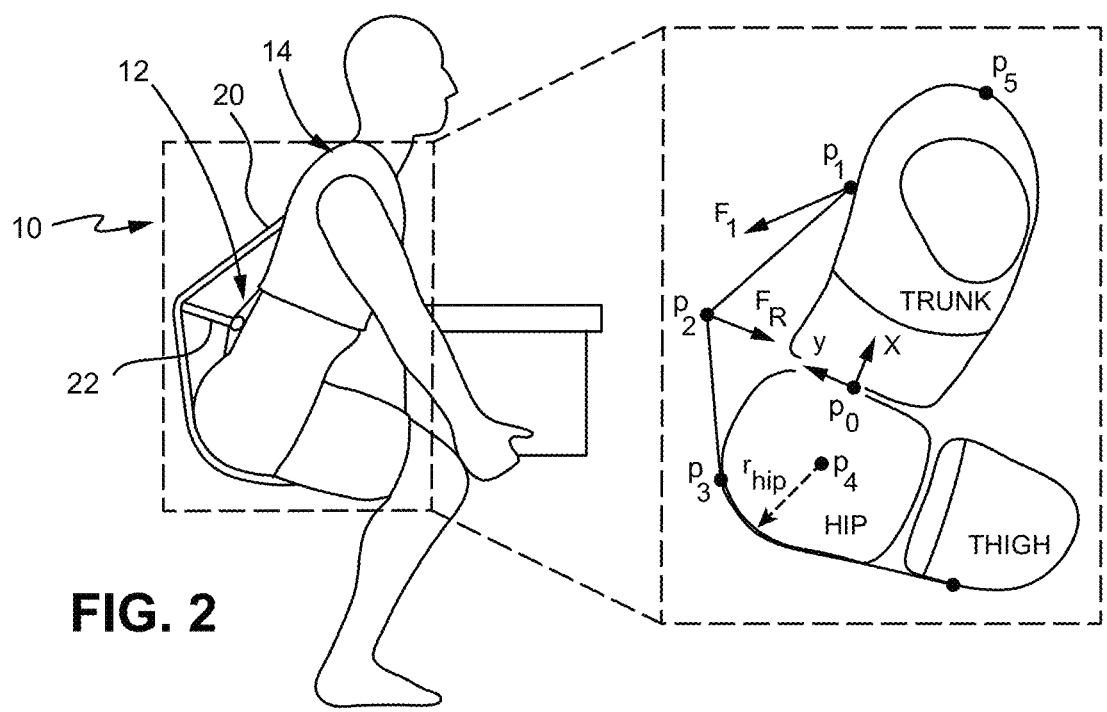
FIG. 2 is a schematic diagram illustrating an exosuit worn by a user and having a moment arm extension system of a hinge-lever design in an extended configuration (as shown in FIG. 1B, along with a closeup of a portion of the exosuit (without the moment arm extension system shown)

Model Objective:
  Characterize the relationship between exosuit parameters (FIG. 2, e.g., $x_1$, $x_2$, $y_2$), and the effective exosuit moment arm and the device-to-body forces (FIG. 2, $F_T$, $F_R$). In FIG. 2, $x_1$ is the x-position of $P_1$ and the attachment point of the elastic member 20 to the trunk interface 16, $x_2$ is the x-position of $P_2$ and the location of the extension mechanism 22 along the spine, and $y_2$ is the y-position of $P_2$ and the offset of the extension mechanism 22 from the back.
  Provide general insights for designing a novel exosuit prototype with an moment arm extension system.
  Identify specific exosuit parameters for prototype implementation.

Model Success Criteria:
  The model characterizes the effects of a subset of exosuit parameters (e.g., $x_1$, $x_2$, $y_2$) on device-to-body forces and exosuit moment arm for a controlled amount of extension torque about the L5S1 joint.
  This model informs the design of a novel moment arm extension system which can reduce device-to-body forces relative to the control exosuit
  Model contribution: The contribution of this model is that it will provide general insight on how device-to-body forces are affected by key exosuit design parameters. Thus, the model will serve as a general tool to inform selection of exosuit design parameters.

Previous models of low-back wearable devices detail the general behavior of each respective device, but none to-date have provided insight about how exosuit design parameters affect device-to-body forces. The purpose of this model is to: i) characterize the effects of select exosuit parameters on device-to-body forces and the exosuit moment arm; and ii) identify specific exosuit parameter values for a functional prototype that can reduce device-to-body forces by 50% compared to the control design.

FIG. 2 is a schematic diagram illustrating exosuit 10 worn by a user and having a moment arm extension system 12 of a hinge-lever design in an extended configuration (as shown in FIG. 1B, along with a closeup of a portion of the exosuit 10 (without the moment arm extension system shown). The inventors have developed a model of the human and exosuit that estimates the device-to-body forces (FIG. 2, $F_T$, $F_R$) needed to create a desired torque ($\tau_{des}$) about the L5S1 joint (FIG. 2, $P_0$). The model is a static, sagittal plane model of the exosuit and human system. The model only considers the sagittal plane because the majority of the biological lumbar moment and exosuit assistive torque ($\tau_{exo}$) are observed in the sagittal plane. This model considers only the exosuit assistance torque created about the L5S1 because it commonly experiences the highest flexion torques along the entire spine. For the main design insights, a model is used which considers the exosuit and human mechanics when the exosuit is engaged (i.e., the moment arm extension system is deployed and elastic band is under tension) and the user is leaning forward. For the scope of this work, an exosuit is modeled that couples the thigh and trunk with an elastic band, which is functionally similar to the inventors' previous designs. The inventors supplement this model by adding routing points (FIG. 2, $P_2$), which redirect the path of the elastic band (FIG. 2). These routing points (which can be thought of as friction-less pulleys) are the core addition to the exosuit which alter the exosuit moment arm and device-to-body forces. The model assumes a constant tension through the elastic band, negligible friction, and rigid thigh, trunk and pelvis segments.

Potential exosuit parameters have been identified which could be manipulated. These include: routing point location along the spine, routing point offset from the skin surface, number of routing points, elastic band attachment point on the trunk interface 14 and the elastic band attachment point on the thigh interface 16. To constrain the scope of this work, the inventors narrowed the options (based on initial physics modeling, physical intuition and expected end-user applications and constraints) to three key parameters: the longitudinal position of the routing point along the spine (FIG. 2, $x_2$), the routing point offset normal to the spine (FIG. 2, $y_2$), and the longitudinal position of the elastic attachment point on the shoulder harness 14 (FIG. 2, $x_1$).

As shown in FIG. 2, the exosuit 10 is comprised of thigh interface 16, trunk interface 14, elastic member/band, 20 and moment arm extension system 12. The thigh interface 16 and trunk interface 14 attach to the thigh and trunk, respectively, and are coupled by elastic band 20. The exosuit 10 creates an assistive force/torque by applying forces at the trunk ($F_T$), the moment arm extension system ($F_R$), the waist (not currently shown) and the thigh (not currently shown). $P_0$ is the L5S1 and model origin. $P_1$ is the point at which the elastic band 20 attaches to the shoulder harness 14 (and applies $F_T$). $P_2$ is the routing point for the elastic band 20 on the moment arm extension system 12 (and where $F_R$ is applied). $P_3$ is the point at which the elastic band makes contact with the waist (simplified as a tangency point with a circle). $P_4$ is the hip center of rotation. The torque created about the L5S1 (exo) by the exosuit 10 is:

$$\tau_{exo} = \tau_T + \tau_R \quad (1)$$

Where $\tau_T$ is the torque created by the device-to-body tension force ($F_T$) on the trunk through the harness 14 and $\tau_R$ is the torque contribution from the device-to-body reaction force ($F_R$) of the moment arm extension system 12 on the body:

$$\tau_T = \vec{r}_{10} \times \vec{F}_T = (\vec{r}_{10} \times \vec{u}_{21}) * f_T \quad (2)$$

$$\tau_R = \vec{r}_{20} \times \vec{F}_R = (\vec{r}_{20} \times (\vec{u}_{32} + \vec{u}_{12})) * f_T \quad (3)$$

In equation 2, $\vec{r}_{10}$ is the position vector from $P_0$ to $P_1$ and $\vec{u}_{21}$ is the unit vector from $P_1$ to $P_2$ and $f_T$ is the tension in the elastic band. In equation 3, $\vec{r}_{20}$ is the position vector from $P_0$ to $P_2$, $\vec{u}_{32}$ is the unit vector from $P_2$ to $P_3$ and $\vec{u}_{12}$ is the unit vector from $P_2$ to $P_1$. This model assumes that the device-to-body forces ($\vec{F}_T$ and $\vec{F}_R$) only create torque about the L5S1 if their line-of-action intersects the body on the right side of the origin (FIG. 2, $P_0$). $P_1$ (the harness anchoring point) is constrained to sit on the right side of the body, and therefore $F_T$ will always create a torque about $P_0$ (assuming $f_t$ 0).

The location of the routing point ($P_2$) is unknown (i.e., to be determined). Moment arm extension system 12 will support this routing point, and the moment arm extension system 12 is allowed to sit anywhere along the back (from the posterior hip to the upper back). However, the inventors assume that the moment arm extension system 12 which supports ($P_2$) will only bear compression loads (i.e., no bending moments). Functionally, this means that the moment arm extension system 12 will sit at the location on the back where $F_R$ intersects the back. $\vec{F}_R$ only creates a flexion (clockwise) torque about $P_0$, and otherwise creates no torque about $P_0$ (equation 4):

$$\tau_R = \begin{cases} \vec{r}_{20} \times \vec{F}_R & \text{if } (\vec{r}_{20} \times (\vec{u}_{32} + \vec{u}_{12})) < 0 \\ 0 & \text{if } (\vec{r}_{20} \times (\vec{u}_{32} + \vec{u}_{12})) \geq 0 \end{cases} \quad (4)$$

There are some cases where $\vec{F}_R$ can create an extension torque about $P_0$, however these are considered to be edge cases that aren't realistic designs.

After minor algebraic manipulations of equations 1, 2 and 3, the following equation 5 is obtained for the tension in the elastic band ($f_T$):

$$f_T = \frac{\tau_{exo}}{\vec{r}_{10} \times \vec{u}_{21} + \vec{r}_{20} \times (\vec{u}_{32} + \vec{u}_{12})} \quad (5)$$

And the following equation 6 is for the magnitude of the reaction force on the body from the moment arm extension system ($f_R$):

$$f_R = \frac{\tau_{exo} \cdot (\vec{u}_{32} + \vec{u}_{12})}{\vec{r}_{10} \times \vec{u}_{21} + \vec{r}_{20} \times (\vec{u}_{32} + \vec{u}_{12})} \quad (6)$$

Equation 5 then can be rearranged to evaluate the moment arm ($R_E$) of the exosuit as it relates to the elastic band tension ($F_T$):

$$\frac{\tau_{exo}}{f_T} = R_E = \vec{r}_{10} \times \vec{u}_{21} + \vec{r}_{20} \times (\vec{u}_{32} + \vec{u}_{12}) \quad (7)$$

The goal of parameter exploration was to characterize how these exosuit parameters ($x_2$, $y_2$ and $x_1$) affect the device-to-body forces ($\vec{F}_T$ and $\vec{F}_R$) and to determine the relative sensitivity of $\vec{F}_T$, $\vec{F}_R$ to these parameters. To characterize the exosuit parameters, a parameter exploration was performed using equations 5, 6 and 7 by varying $x_1$, $x_2$ and $y_2$ across their respective domains (see Table 1 below) while holding the desired exo torque constant at 25 Nm ($\tau_{desired} = \tau_{exo} = 25$ Nm). To determine the sensitivity of the device-to-body forces to changes in the exosuit parameters, the partial derivatives of $\vec{F}_T$, $\vec{F}_R$ was calculated with respect to each parameter ($x_1$, $x_2$ and $y_2$).

TABLE 1

Top: Domain of the parameters to the L5S1 joint (coordinate system defined in FIG. 2). Bottom: Anthropometric measurements to scale the model. Values are based on data from ANSURII

| Parameter | Minimum | Maximum |
|---|---|---|
| $x_1$ | $x_0$ | $d_{50}$ |
| $x_2$ | $x_4 - r_{hip}$ | $d_{50}$ |
| $y_2$ | $d_{skin}$ | $d_{skin} + 0.2$ m |

| Measurement | Value |
|---|---|
| $r_{hip}$ | $0.1 \pm x$ m |
| $d_{40}$ | $0.135 \pm x$ m |
| $d_{50}$ | $0.4 \pm x$ m |
| $d_{skin}$ | $0.08 \pm x$ m |

The goal of parameter selection process is to use the insight gained from the model to identify specific parameter values to achieve this design goal. The design goal for this specific exemplary implementation was to reduce $f_T$ by 50% while minimizing the distance the moment arm extension system protrudes from the back (i.e., $y_2$). First, anthropometric values were selected to scale the model to a 50$^{th}$ percentile male based on data from the 2012 US Army Anthropometric Survey (ANSURII) (Table 1). Next, equation 5 was used to determine the baseline elastic band tension force ($f_{T_{base}}$) required to create 25 Nm of assistance torque. Next, the inventors allow $$f_T = \frac{1}{2} f_{T_{base}}$$

and $\tau_{exo} = 25$ Nm in equation 5, and treated the equation as an implicit function with $x_2$, $y_2$ and $x_1$ as variables. The implicit function defines a 3D surface in the parameter space which satisfies the constraint that $$f_T = \frac{1}{2} f_{T_{base}}.$$

Next, an anchoring point ($x_1$) is chosen that will work best for these particular design constraints. Finally, within the remaining parameter space, the minimum $y_2$ value and the corresponding $x_2$ value are found.

Design Objective: An exosuit prototype with a moment arm extension system will be designed and built that extends passively (i.e., no powered motor) when the device is engaged (increasing the exosuit moment arm), and collapses when the device is disengaged (maintaining a low profile). The prototype may optionally have a clutch that the wearer can use to engage and disengage the assistance spring (i.e., elastic member) and extensible moment arm on-demand.

Design success criteria: Develop a fully functional exosuit prototype with moment arm extension system and an optional clutch.

Design contribution: The design contribution of this work is a novel exosuit design that is low-profile and clothing-like which provides the same magnitude of assistance with lower device-to-body forces than the previous exosuit designs.

Exosuit Design: A primary goal of the exosuit design was to provide 25 Nm of assistance torque ($\tau_{exo}$) with 50% lower device-to-body force at the shoulders. Additionally, it was required that the exosuit have an engaged and disengaged mode. When the exosuit is disengaged, the wearer should be uninhibited by the exosuit and should be able to perform common daily tasks, such as sitting.

The core softgoods components of the exosuit 10 are the shoulder harness 14, a waist belt 18 (as, for example, shown in FIGS. 8A-8B), and two thigh sleeves 16. The shoulder harness 14 transmits tension forces in the elastic bands 20 along the back to the wearers trunk and shoulders. The moment arm extension system 12 is secured to the waist belt 18 which holds the moment arm extension system 12 in the correct position and comfortably transfers the reaction forces on the moment arm extension system 12 to the back. The thigh sleeves 16 transmit tension forces in the elastic bands 20 to the wearers thighs. Elastic bands 20 with an approximate stiffness of 500 N/m, are connected to the shoulder harness 14 and the thigh sleeves 16 using standard or custom connectors. The elastic bands 20 are routed through the moment arm extension system 12.

Using the results from the parameter selection process, design details (i.e., specific values for $x_1$, $x_2$ and $y_2$) are provided, and exosuit design parameters are scaled. The value for $x_1$ designates the location on the exosuit harness 14 at which the elastic band 20 is anchored. Therefore, the elastic bands 20 are mounted on the harness 14 at the point defined $x_1$. The value for $x_2$ specifies where the center of the moment arm extension system 12 will sit on the back. The moment arm extension system 12 is secured to the exosuit 10 with a waist belt 18 (which may attach to the harness 14) and is situated along the back according to $x_2$. Finally, the $y_2$ value specifies the extended length of the moment arm extension system.

Moment Arm Extension System Design: The goal of this particular exosuit prototype is to reduce the device-to-body forces by 50% (specifically $f_T$) for a 50$^{th}$ percentile male. The model is scaled with the anthropometric measurements and design criteria to identify the particular exosuit parameters (see Parameter Selection above). Another goal is for the design to be as unobtrusive as possible, meaning that the addition of the moment arm extension system 12 should not add significant bulk to the exosuit, nor make it more difficult to do common activities (e.g., sit) when wearing the exosuit.

Parameter Sensitivity: To accommodate for variations in the exosuit parameters, resulting from soft-tissue and fabric deformations, minor adjustments are made in the exosuit parameters. First, the inventors note that the parameters which are most susceptible to variation due to soft-tissue and fabric deformations are the $x_1$ and $y_2$. Only a negligible fraction of $F_R$ is applied along the x-axis on the moment arm extension system. Therefore, it is assumed that motion of the moment arm extension system 12 along the spine will be negligible. However, the inventors note that $f_T$ and $f_R$ may cause minor displacements in $y_2$ as the moment arm extension system 12 is pushed into the back by $f_R$ and minor displacements as $f_T$ pulls back on $x_1$. Based on pilot data which approximates the tissue and fabric stiffness, the inventors can estimate the displacements experienced in $x_1$ and $y_2$ during normal use of the exosuit. Based on these expected displacements, $x_1$ and $y_2$ are adjusted accordingly.

To achieve a targeted level of $\tau_{exo}$, a specific elastic band stiffness is needed which will deform according to the following equation $dS = r_{Hip} d\theta$ where $dS$ is elastic band displacement, $r_{Hip}$ is the radius of the hip, and $d\theta$ is the change in the angle between the thigh and the trunk. For this particular application, it is desired to achieve $\tau_{exo} = 25$ Nm when the user is squatting to pick up a box from the ground.

Case-study objective: design implementation/proof-of-concept will be demonstrated with case-study (N=1). It will also be demonstrated that the wearer can perform common tasks without interference (e.g., sitting and plyometrics) while wearing the novel exosuit. Finally, it will be demonstrate that the novel exosuit prototype can provide a similar magnitude of assistance with lower device-to-body forces vs. the control version of the exosuit (without a moment arm extension system).

Case-Study Success Criteria:
 Users demonstrate the ability to perform daily task(s) (e.g., sitting, walking) without interference from novel exosuit. User feedback on comfort will be rated with a Likert scale survey and bench-marked against the control exosuit.
 Novel exosuit provides comparable torque assistance with lower-on body forces during semi-controlled lifting and leaning tasks compared to control exosuit. Torque assistance and device-to-body forces will be estimated with a combination of motion capture and force sensing.

Case-study contribution: The contribution of this case-study is demonstrating the biomechanical function of the novel exosuit design which provides the same magnitude of assistance but with lower device-to-body forces (and higher comfort). For the case-study, subjects performed functional and simulated lifting and leaning exercises, common daily movements and mobility movements.

4. Results
4.1 Modeling

Figure 4:
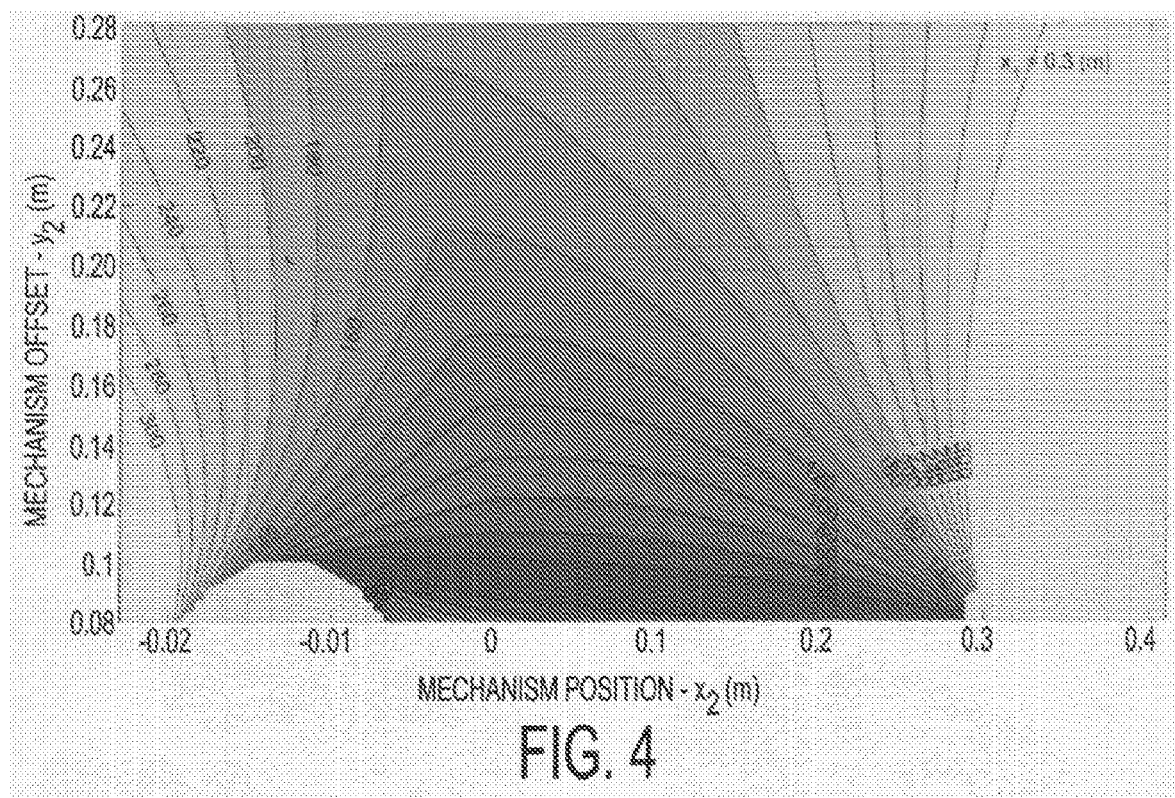
FIG. 4 is a plot illustrating device-to-body force $F_R$ calculated from equation 6 (below) across the mechanism position ($x_2$) and mechanism offset ($y_2$) parameter domain specified in Table 1 (below) and with a constant $x_1$=0.3 m.
Figure 5:
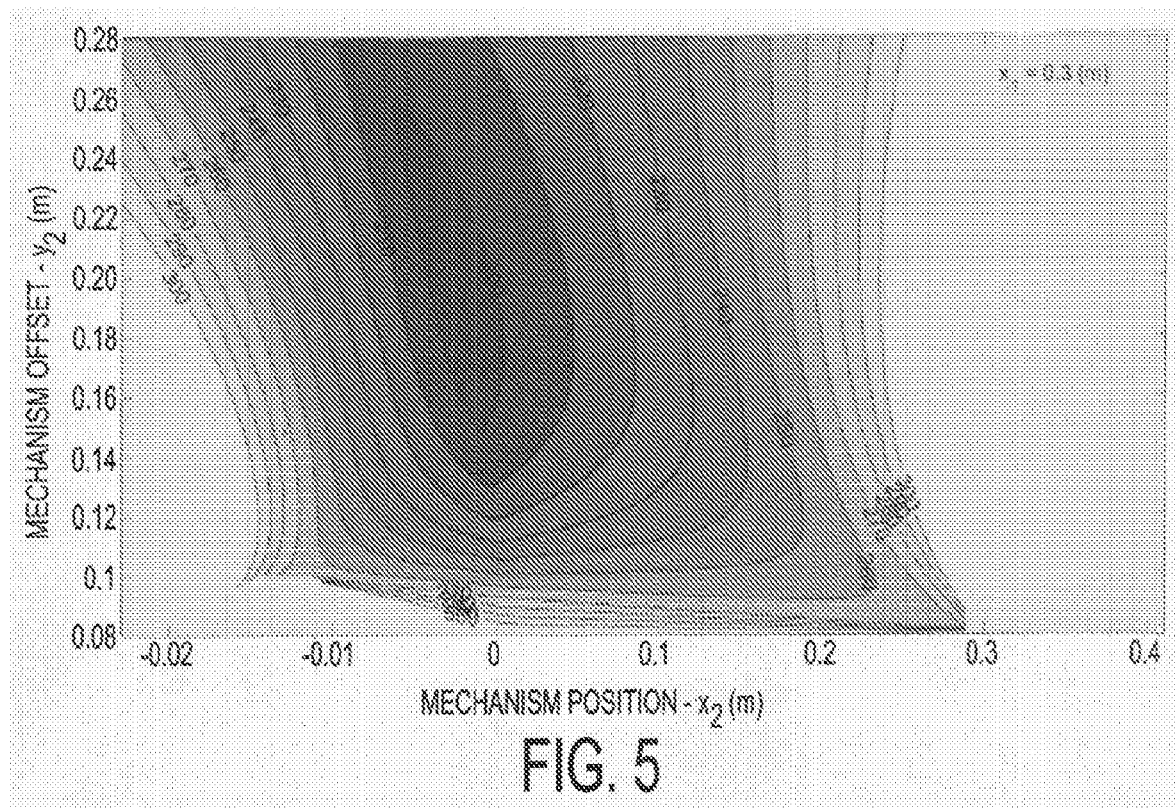
FIG. 5 is a plot illustrating magnitude of device-to-body forces ($\sqrt{f_T^2+f_R^2}$) across the mechanism position ($x_2$) and mechanism offset ($y_2$) parameter domain specified in Table 1 and with a constant $x_1$=0.3 m.

Within the exploration parameter space defined in Table 1, the exosuit tension force ($f_T$) ranged from 115 to ∞ (FIG. 4). The minimum $f_T$ was observed at $x_2$=−0.13, $y_2$=0.28 (maximum value in domain), and $x_1$=0.41 (maximum value in domain). $F_R$ ranged from 0 to ∞ (FIG. 5). $f_R$ was zero for any parameter combinations where $\vec{u}_{12} \times \vec{u}_{23} < 0$. $f_T$ and $f_R$ approached ∞ as equation 7 or the denominators of equations 5 and 6 approached zero. $f_T$ and $f_R$ values are truncated at 400 N for practical and presentation purposes.

The partial derivatives of $x_2$, $y_2$ and $x_1$ with respect to $F_T$ were 235.18, −390.13 and 0.00 respectively. The partial derivatives of $x_2$, $y_2$ and $x_1$ with respect to $F_R$ were 48.33, 571.70 and −156.79 respectively. All partial derivatives were calculated at a representative point in the parameter space: $x_1$=0.3 m, $x_2$=0 m, $y_2$=0.2 m.

Figure 3:
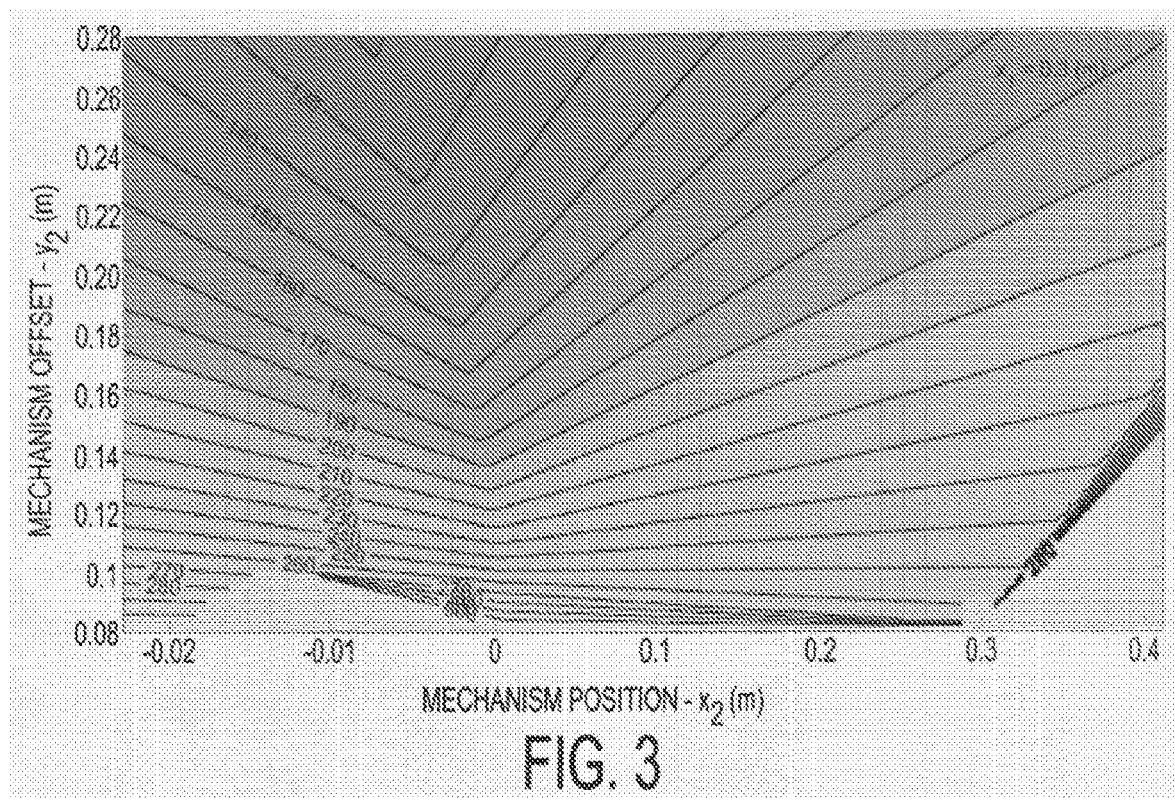
FIG. 3 is a plot illustrating device-to-body force $F_T$ calculated from equation 5 (below) across the mechanism position ($x_2$) and mechanism offset ($y_2$) parameter domain specified in Table 1 (below) and with a constant $x_1$=0.3 m.

FIG. 3 illustrates device-to-body force $F_T$ calculated from equation 5 across the $x_2$ and $y_2$ parameter domain specified in Table 1. All points along a contour line denote parameter combinations with a constant $f_T$ in Newtons. The location of the routing point $P_2$ are the axes of the plot ($x_2$ along the x-axis and $y_2$ along the y-axis). This contour plot is evaluated for different values of $x_1$=0.3 m. The gray area in the contour plots indicate invalid parameter combinations.

FIG. 4 illustrates device-to-body force $F_R$ calculated from equation 6 across the $x_2$ and $y_2$ parameter domain specified in Table 1. All points along a contour line denote parameter combinations with a constant $F_R$. The location of the routing point $P_2$ are the axes of each subplot ($x_2$ along the x-axis and $y_2$ along the y-axis). The gray area in the contour plots indicate invalid parameter combinations.

FIG. 5 illustrates magnitude of device-to-body forces ($\sqrt{f_T^2 + f_R^2}$) across the $x_2$ and $y_2$ parameter domain specific in Table 1 and with a constant $x_1$=0.3 m. All points along a single contour line denote parameter combinations with a constant device-to-body force magnitude. There is a local minimum at $x_2$=0.0 m and $y_2$=0.2 m, denoting where the device-to-body force magnitude is the lowest for 25 Nm of torque and $x_1$=0.3 m. The gray area in the contour plots indicate invalid parameter combinations.

TABLE 2

Sensitivity of $F_T$ and $F_R$ to exosuit parameters: partial derivatives presented in Table 2 were calculated numerically at a single point in the parameter space ($x_1$ = 0.3 m, $x_2$ = 0 m, $y_2$ = 0.2 m)

$$\begin{bmatrix} \frac{\delta F_T}{\delta x_2} & \frac{\delta F_R}{\delta x_2} \\ \frac{\delta F_T}{\delta y_2} & \frac{\delta F_R}{\delta y_2} \\ \frac{\delta F_T}{\delta x_1} & \frac{\delta F_R}{\delta x_1} \end{bmatrix} = \begin{bmatrix} 235.18 & 48.33 \\ -390.13 & 571.70 \\ 0.00 & -156.79 \end{bmatrix}$$

4.2 Parameter Selection

With the model scaled to the 50$^{th}$ percentile male anthropometrics (Table 1), $f_{t_{base}}$ =300 N, the target $f_T$ was 150 N. Based on design constraints related to the shoulder harness, it was determined that the $x_1$ position should be approximately 0.2 m. With $f_T$ and $x_1$ defined, the design is constrained to a single contour line (e.g., FIG. 3), which identifies which combinations of $x_2$ and $y_2$ are valid. The combination of $x_2$ and $y_2$ with the smallest $y_2$ was chosen to minimize the footprint of the exosuit. The chosen parameters were $x_2$=0.0 m, $y_2$=0.18 m, $x_1$=0.2 m. The partial derivatives at this point are shown in Table 3 below.

TABLE 3

Sensitivity of $R_E$, $F_T$ and $F_R$ to exosuit parameters: partial derivatives presented in Table 3 were calculated numerically for the parameters selected for the design implementation ($x_1$ = 0.2 m, $x_2$ = 0 m, $y_2$ = 0.18 m)

$$\begin{bmatrix} \frac{\delta F_T}{\delta x_2} & \frac{\delta F_R}{\delta x_2} \\ \frac{\delta F_T}{\delta y_2} & \frac{\delta F_R}{\delta y_2} \\ \frac{\delta F_T}{\delta x_1} & \frac{\delta F_R}{\delta x_1} \end{bmatrix} = \begin{bmatrix} -5.00 & -62.74 \\ -523.28 & 692.47 \\ -81.68 & -349.51 \end{bmatrix}$$

5. Discussion, Modeling, and Parameter Exploration Summary

Based on results from the parameter exploration, the inventors found that the parameters $y_2$ and $x_2$ had significant effects on $f_T$ and $f_R$ while $x_1$ only had a moderate effect on $f_R$. The main effect of $x_2$ was to change the orientation of $F_R$. The best values for $x_2$ which resulted in the lowest device-to-body forces were near or slightly behind the x-position of the L5S1. The main effect of $y_2$ was to change $f_T$ and $f_R$ where increasing $y_2$ increased $f_R$ while reducing $f_T$. The benefits of extending $y_2$ farther plateau around $y_2$=0.28 m. The main effect of increasing $x_1$ was to decrease $f_R$. However, for values beyond $x_1$=0.2 m, the effects on $F_R$ were minor. The location of the harness anchoring point ($x_1$) should be at least 0.2 m>$x_0$. The optimal parameter combinations occur when $f_R$ intersects $P_0$ or the L5S1 joint. This relationship between the parameters is defined implicitly by $(\vec{r}_{20} \times (\vec{u}_{32} + \vec{u}_{12}))=0$.

Routing Point Position: $x_2$

From the parameter exploration, the optimal routing point position ($x_2$) was found to be near or slightly below the L5S1 joint ($x_0$). As an example, if it is assumed that it is desired to reduce $t_F$ to 140 N with $x_1$=0.3 m while minimizing $y_2$, one would look for the point on the 140 N contour in FIG. 3 with the smallest $y_2$ value, and would find that the corresponding $x_2$ position is near or slightly behind the L5S1 joint. This behavior holds true while $x_1 \geq 0.2$ m. For $x_1 \leq 0.2$ m, one would find that the optimal $x_2$ values lie at or slightly above the L5S1 joint. This behavior boils down to the fact that the optimal parameter combinations are defined by ($\vec{r}_{20} \times (\vec{u}_{32} + \vec{u}_{12})) = 0$, which implies that $F_R$ intersects $P_0$. Increasing or decreasing $x_2$ therefore has the effect of moving $f_R$ above or below the L5S1 joint, both which reduce the effective moment arm of the exosuit. Similar to $f_T$, the optimal $x_2$ values for $f_R$ are near or slightly behind $P_0$ (FIG. 3). When $x_2 \geq x_1$, the values of $f_T$ and $f_R$ begin to increase significantly. This suggests that $x_2$ shoulder stay behind $x_1$. From the sensitivity analysis one can estimate that for ±1 cm of variation in $x_2$, $f_T$ could vary by ±2.35 N, which is a small percentage of realistic $f_T$ magnitudes (<5%). Similarly $f_R$ could vary by ±0.48 N which is also a small percentage of $f_R$ (<5%). Note that these numbers are most reflective for parameter values near $x_2$=0.0, $y_2$=0.2 and $x_1$=0.3. Overall this sensitivity analysis suggests that minor drift in $x_2$ should not have significant effects on the mechanics of the exosuit. This is a useful characteristic because there may be minor differences in the positioning of the device when it is donned and doffed, thus this suggests that minor daily drifting of the exosuit will not affect its performance.

Routing Point Offset: $y_2$

Based on the parameter exploration, $y_2$ appears to have a significant effect on $f_T$ and $f_R$. Increasing $y_2$ tended to decrease $F_T$ for all of the explored parameter space (FIG. 3). Unlike for $x_2$, there does not appear to be an optimal $y_2$ across the whole parameter space value because increasing $y_2$ further, continues to reduce $f_T$. With some additional assumptions to the model (see equations X-Z in the appendix), one can estimate that 80% of reduction has been achieved in $f_T$ if one allows $\|\vec{r}_{10}\| = \|\vec{r}_{20}\|$. Functionally, this means that there are diminishing benefit (in terms of reducing $f_T$), when increasing $\|y_2\|$ beyond $\|x_1\|$. With the more realistic model based on equation 7, one finds that there is very little benefit in extending $y_2$ beyond 0.28 m as $f_T$ appears to plateau near 115 N. Despite this plateauing behavior, one can identify the "optimal" $y_2$ for a targeted $f_T$. For example, if one wanted to reduce $t_F$ to 140 N with $x_1$=0.3 m, one would locate a minimum value of $y_2$ which sits on the 140 N contour. The relationship between $y_2$ and $f_R$ is nearly the opposite the relationship between $y_2$ and $f_R$. As $y_2$ increases $f_R$ also increases. This relationship holds when $x_4 \leq x_2 \leq x_1$ (FIG. 4), but outside of this range, increasing $y_2$ has little effect on $f_T$. Based on the sensitivity analysis and FIGS. 3 and 4, one can see that $y_2$ has significant effects on $f_T$ and $f_R$. A ±1 cm change in $y_2$ would yield a 3.9 N and 5.7 N change in $f_T$ and $f_R$, respectively. While these changes are only a small fraction of the magnitudes relevant for this work, the values for $f_T$ are nearly double that of $x_2$ and the values of $f_R$ are over 10× that of $x_2$. This suggests that outcomes are more sensitive to $y_2$ than they are to $x_2$. For design purposes, this suggests that one may need to accommodate for potential variation in $y_2$ by increasing its value slightly in anticipation of $y_2$ decreasing slightly during exosuit use. As the exosuit is engaged, the reaction force $f_R$ will actively push the moment arm extension system into the soft-tissue of the back, which may temporarily reduce $y_2$ when the exosuit is in use.

Harness Anchoring Point: $x_1$

From the parameter exploration, as long as the value of $x_1$ 0.2 m, then it appears to only play a minor role in $f_t$ and $f_R$. When $x_1$ is near $x_2$, then it appears to have greater influence on $f_T$ and $f_R$. In general, however there is no benefit, in terms of reducing device-to-body forces, to bringing $x_1$ close to $P_0$. In fact, it appears that having as large an $x_1$ as is possible (i.e., given design constraints related to attaching to the harness/shoulders 14) is better for increasing the moment arm and decreasing device-to-body forces. Additionally, attaching farther up on the harness 14 has the benefit of creating greater extension torque about more superior levels of the spine. Based on the sensitivity analysis, $x_1$ only has an effect on $f_R$ (assuming that one is at or near the point in parameter space identified in Table 2). Based on the partial derivative at this point, a ±1 cm change in $x_1$ would result in a ±1.57 N change in $f_R$ which is roughly one third of the change induced by $y_2$. Overall these findings suggest that as long as $x_1$ is ≥0.2 m, then it has little effect on the moment arm or device-to-body forces.

Optimal Parameter Combinations

If a goal of the design is to reduce device-to-body forces and the device footprint (i.e., $y_2$), it appears that the best combination of parameters coincide with cases when equation 3 is equal to zero. This implies that the torque contribution from $f_R$ is zero, because the vector intersects the axis of rotation of the L5S1 joint. This can be explained intuitively if one considers the other two cases when $F_R$ doesn't intersect L5S1. For these cases one assumes $x_1$ and $y_2$ are constant. For case 1, one moves $x_2$ in the negative direction until $f_R$ is intersecting a point to the left of the L5S1 joint. $f_R$ is creating no torque about L5S1, and by moving $x_2$ to the left, the moment arm is actually effectively reduced, as $\vec{r}_{10}$ and $\vec{F}_R$ is made less orthogonal. In case 2, one moves $x_2$ in the positive direction until $f_R$ is intersecting a point to the right of the L5S1 joint. $f_R$ is now creating a flexion torque (opposite what one would want the exosuit to do) about the L5S1 joint. This also has the net effect of reducing the moment arm because now $f_R$ is creating a torque which is countering the extension torque of $f_T$. The net result is that the best parameters are such that $f_R$ intersects the L5S1 joint.

Figure 6A:
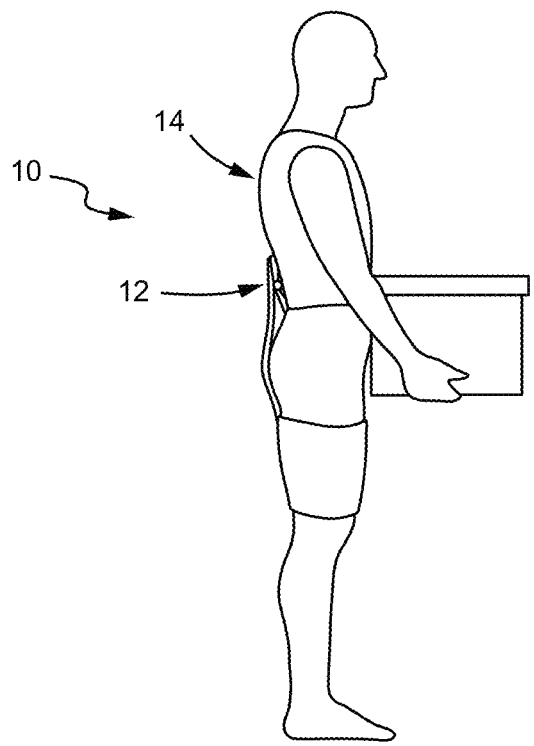
FIGS. 6A-6B are schematic diagrams illustrating an exosuit worn by a user and having a moment arm extension system of a hinge-lever design (of the type shown in FIGS. 1A and 1B) connected to the harness portion of the exosuit, in a collapsed configuration and extended configuration, respectively.
Figure 6B:
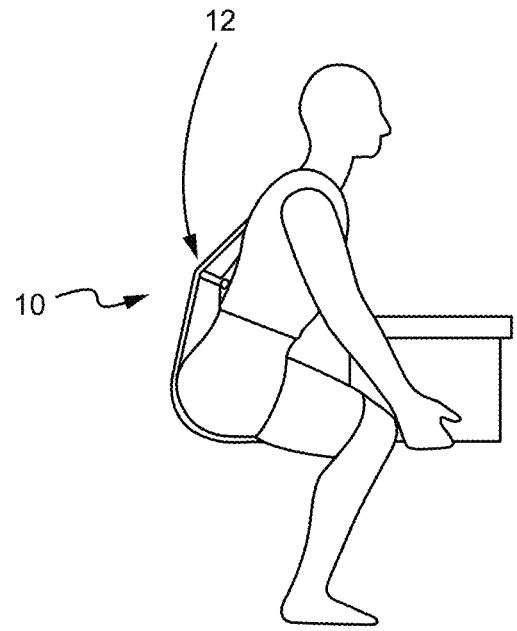

FIGS. 6A-6B are schematic diagrams illustrating an exosuit worn by a user and having a moment arm extension system of a hinge-lever design (of the type shown in FIGS. 1A and 1B) connected to the harness portion of the exosuit, in a collapsed configuration and extended configuration, respectively.

Figure 7A:
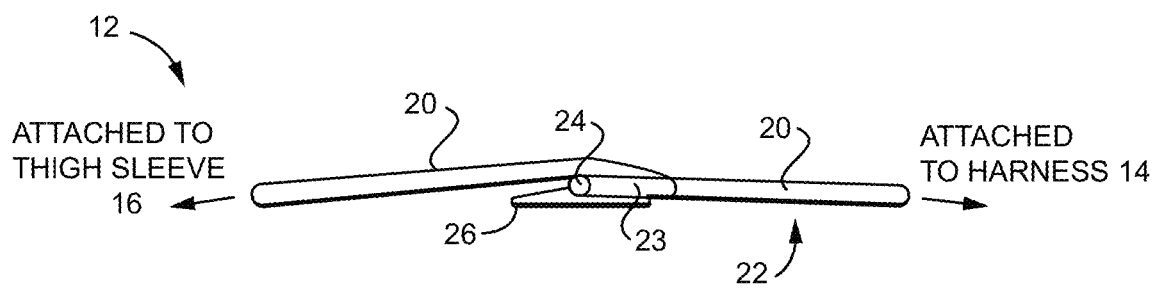
FIGS. 7A-7B are schematic diagrams illustrating a moment arm extension system of a hinge-lever design in a collapsed configuration and extended configuration, respectively.
Figure 7B:
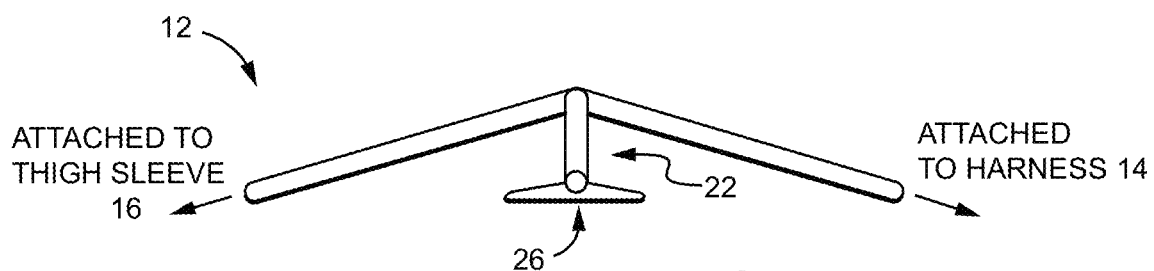

FIGS. 7A-7B are schematic diagrams illustrating an enlarged view of moment arm extension system 12 of a hinge-lever design in a collapsed configuration and extended configuration, respectively. As seen in FIGS. 7A and 7B, moment arm extension system 12 may comprise an extendable member 22, that may comprise a lever 23, a hinge 24, and a base 26. In FIG. 7A, moment arm extension system 12 is shown disengaged (when forces are below threshold). In FIG. 7B, moment arm extension system 12 is shown engaged (when forces are above threshold).

Figure 8A:
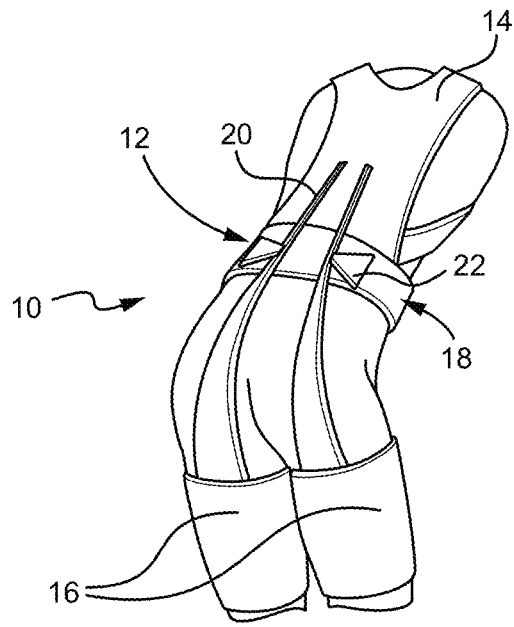
FIGS. 8A-8D are schematic diagrams illustrating an exosuit worn by a user and having a moment arm extension system of a laterally opening hinge-lever design connected to a waistband portion of the exosuit, in a collapsed configuration (FIG. 8A) and extended configuration (FIGS. 8B-8D)
Figure 8B:
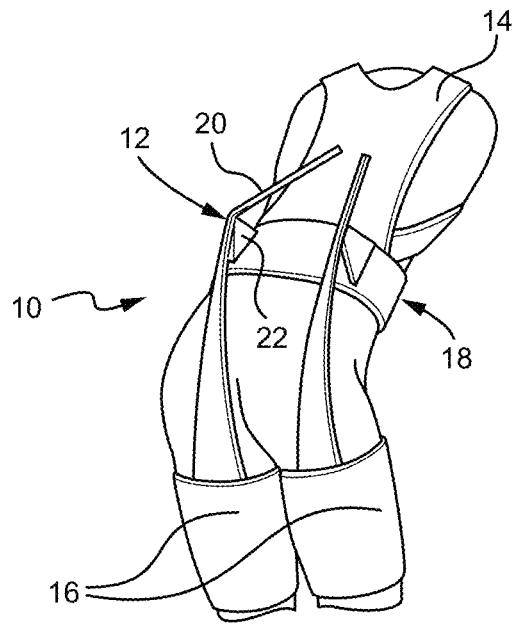
Figure 8C:
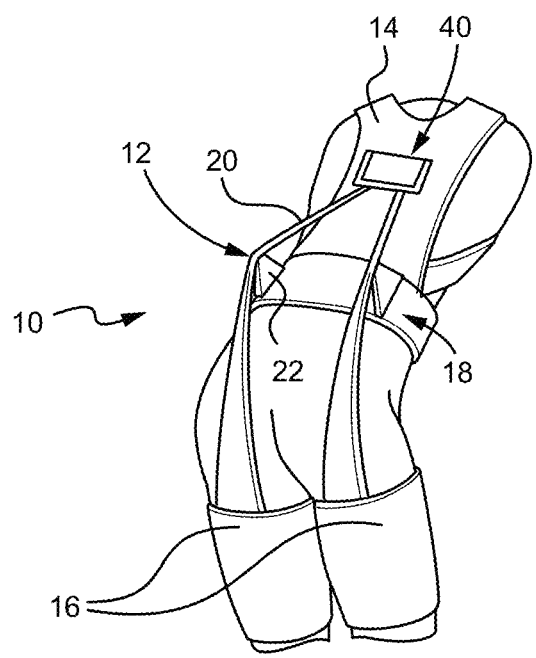
Figure 8D:
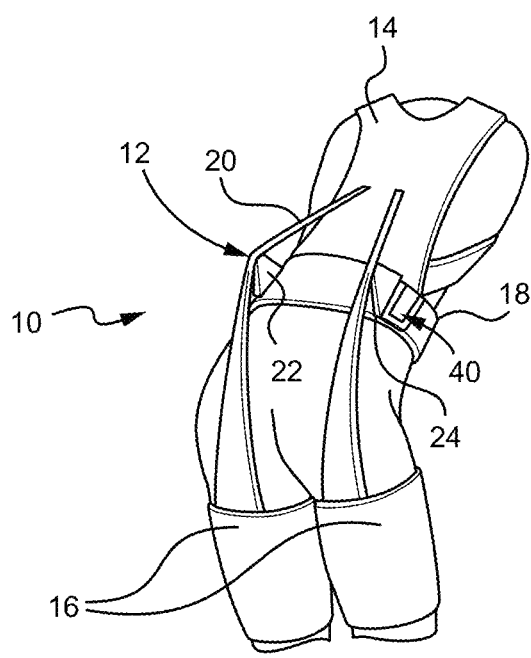

FIG. 8A-8D are schematic diagrams illustrating exosuit 10 worn by a user and having moment arm extension system 12 of a laterally opening hinge-lever design connected to waistband portion 18 of the exosuit 10, in a collapsed configuration (FIG. 8A) and extended configuration (FIG. 8B-8D).

With respect to FIG. 8A-8B, tension in the cables (elastic members 20) is used to apply a lateral tension force on the extendable members 22 (e.g. levers) on the low back. The tension force causes the extendable members 22 to flare out, thereby moving the elastic bands 20 farther away from the back and extending/increasing the moment arm. In other embodiments (FIG. 8C-8D), the hinged levers or extendable members 22 are controlled by a single motor or multiple motors or other powered actuators to switch modes between low-profile (collapsed) and extended, or to extend further, to generate assistive power (e.g., net positive mechanical work) or greater assistive power, to augment movement. The hinge-lever axis could be oriented in various alternative directions, and could also be actuated by manual user input. In FIG. 8C, the powered exosuit has an actuator 40 located mid-back and pulls along the elastic member. Whereas, in FIG. 8D, the actuator 40 is located at each hinge 24, wherein each actuator directly controls the respective lever.

Figure 9A:
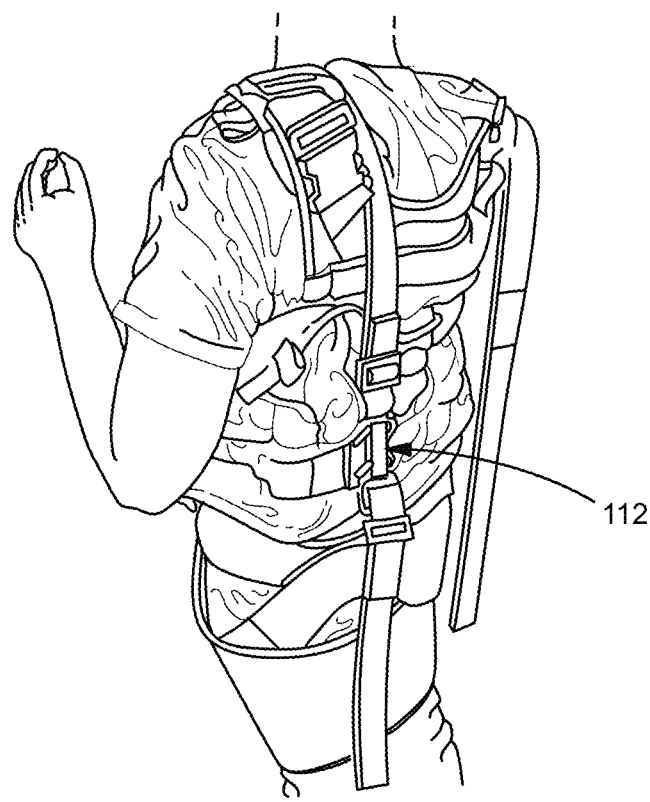
FIGS. 9A-9B are diagrams illustrating an exosuit worn by a user and having a moment arm extension system of a four-bar/link design in a collapsed/disengaged configuration and extended/engaged configuration, respectively.
Figure 9B:
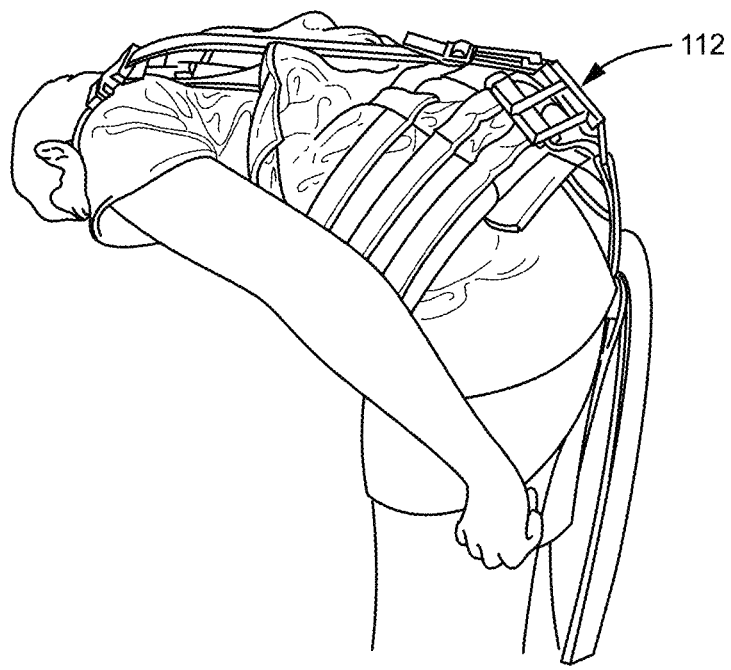

FIGS. 9A-9B are diagrams illustrating an exosuit worn by a user and having a moment arm extension system 112 of a four-bar/link design in a collapsed/disengaged configuration and extended/engaged configuration, respectively.

Figure 10A:
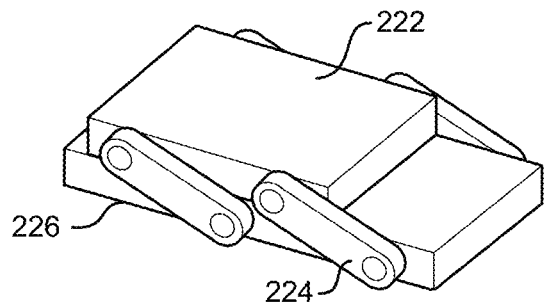
FIGS. 10A-10B are schematic diagrams illustrating a moment arm extension system of a four-bar design in a collapsed configuration and extended configuration, respectively.
Figure 10B:
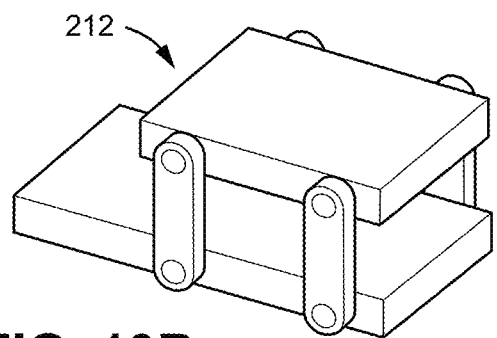

FIGS. 10A-10B are schematic diagrams illustrating a moment arm extension system 212 of a four-bar design in a collapsed configuration and extended configuration, respectively. The moment arm extension system 212 may comprise an extendable member 222, links 224, and a base 226. In another embodiment, the hinged links are controlled by a single motor or multiple motors or other powered actuators or manual user input to switch modes between low-profile (collapsed) and extended, or to extend further, to generate assistive power (e.g., net positive mechanical work) or greater assistive power, to augment movement.

Figure 11:
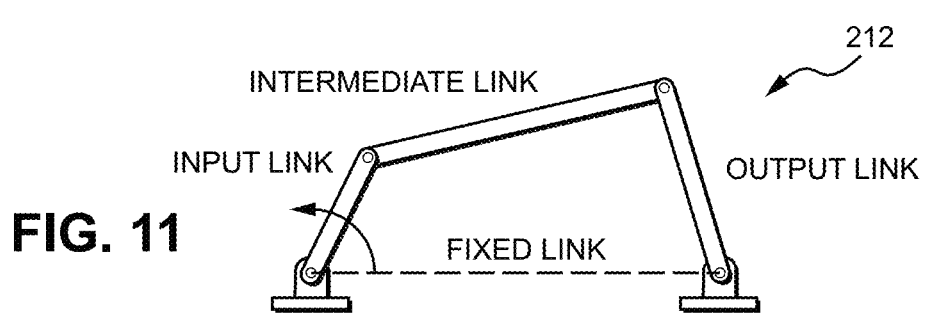
FIG. 11 is a side schematic diagram illustrating a moment arm extension system of a four-bar design in an extended configuration.

FIG. 11 is a side schematic diagram illustrating moment arm extension system 212 of a four-bar design in an extended configuration. The links in FIG. 11 may be representative of the elements shown in FIGS. 10A-10B. In particular, the fixed link and intermediate link in FIG. 11 correspond to the base 226 and extendable member 222, respectively, in FIGS. 10A-10B. The input and output links (which may be reversed) in FIG. 11 correspond to any of the links 224 in FIGS. 10A-10B. Also, when the moment arm extension system in FIGS. 10A-10B is referred to as the "four-bar" design, each pair of links that are connected to opposite edges of the extendable member are considered a "single link", thus the "four bars" are the base, two pairs of links, and the extendable member. Alternatively, the moment arm extension system in FIGS. 10A-10B may have less links (e.g., only one link) in place of both link pairs, or moment arm extension system may have a greater number of links or pairs of links. Some or all the links may be any movable element or joint that allows movement with respect to an adjacent link.

Figure 12:
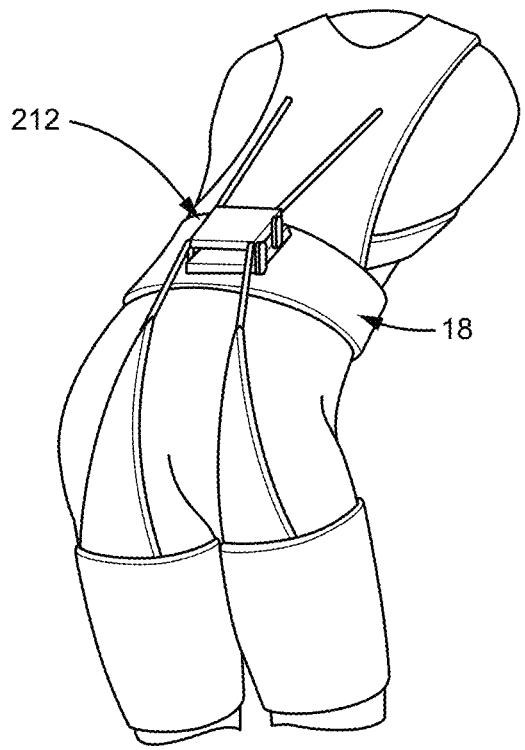
FIG. 12 is a schematic diagram illustrating an exosuit worn by a user and having a moment arm extension system of a four-bar design connected to a waistband portion of the exosuit, in an extended configuration.

FIG. 12 is a schematic diagram illustrating an exosuit worn by a user and having moment arm extension system 212 of a four-bar design connected to a waistband portion 18 of the exosuit, in an extended configuration.

With respect to FIGS. 10A-12, as the user leans forward, the elastic bands (between the thigh sleeves and the moment arm extension system) stretch and apply tension to the moment arm extension system comprising a four-bar/link mechanism, causing an extendable member of the four-bar mechanism to extend away from the back, thereby moving the elastic bands away from the back and extending/increasing the moment arm. When the four-bar/link mechanism lies flat in the collapsed configuration, it may be approximately 2 to 5 cm thick. When the four-bar/link mechanism is extended in the extended configuration, it may be approximately 10 to 25 cm thick.

Figure 13A:
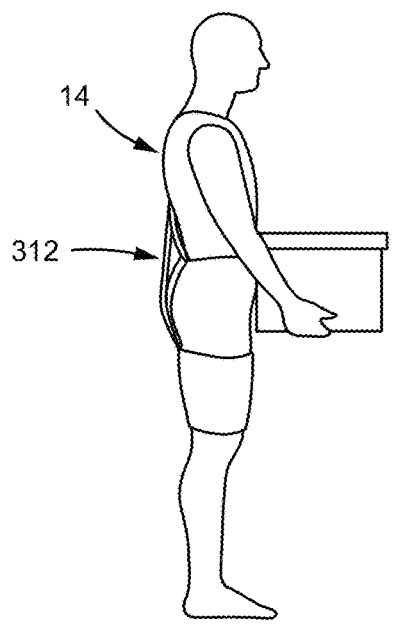
FIGS. 13A-13B are schematic diagrams illustrating an exosuit worn by a user and having a moment arm extension system of a flexible member design connected to the harness portion of the exosuit, in a collapsed configuration and extended configuration, respectively.
Figure 13B:
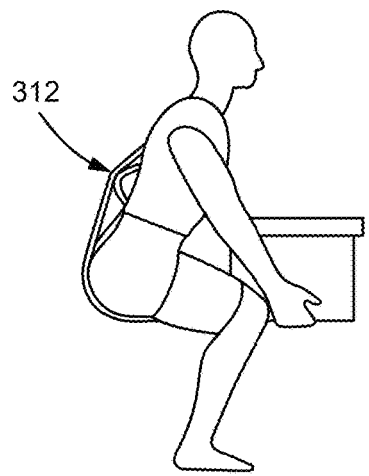

FIGS. 13A-13B are schematic diagrams illustrating an exosuit worn by a user and having a moment arm extension system 312 of a flexible member design connected to the harness portion of the exosuit, in a collapsed configuration and extended configuration, respectively.

Figure 14A:
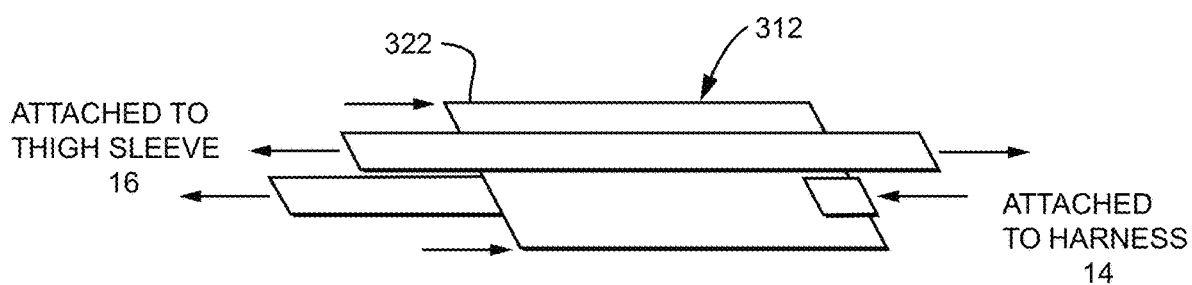
FIGS. 14A-14B are schematic diagrams illustrating a moment arm extension system of a flexible member design in a collapsed configuration and extended configuration, respectively.
Figure 14B:
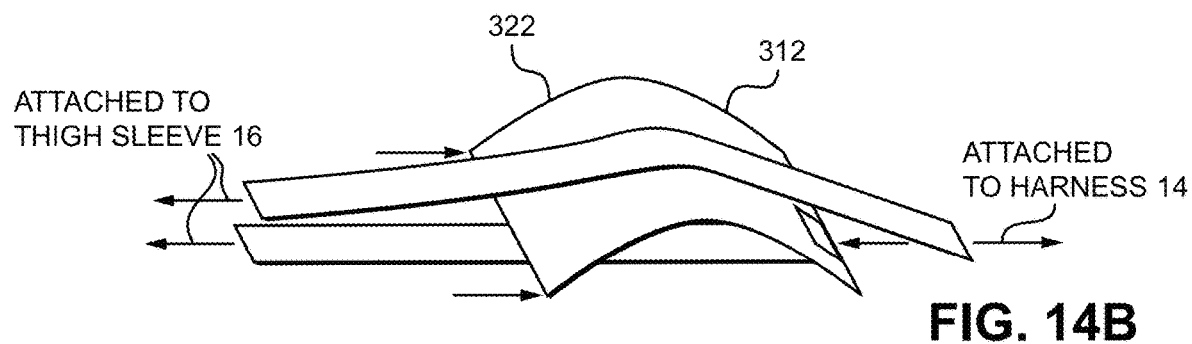

FIGS. 14A-14B are schematic diagrams illustrating moment arm extension system 312 of a flexible member design in a collapsed configuration (disengaged when forces are below threshold) and extended configuration, respectively. Moment arm extension system 312 may comprise a flexible extendable member 322, e.g. a thin steel spring.

Figure 15A:
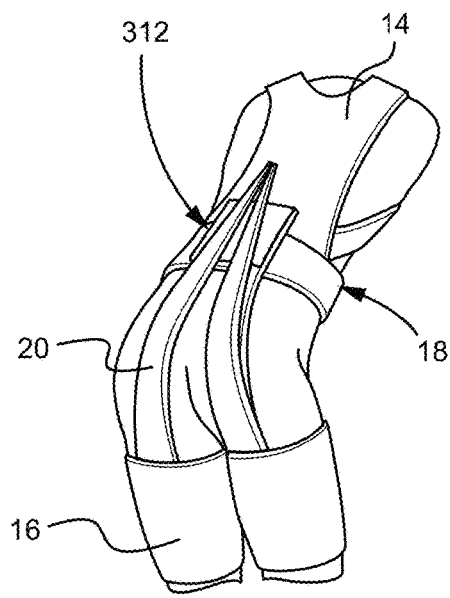
FIGS. 15A-15B are schematic diagrams illustrating an exosuit worn by a user and having a moment arm extension system of a flexible member design connected to a waistband portion of the exosuit, in a collapsed configuration and extended configuration, respectively.
Figure 15B:
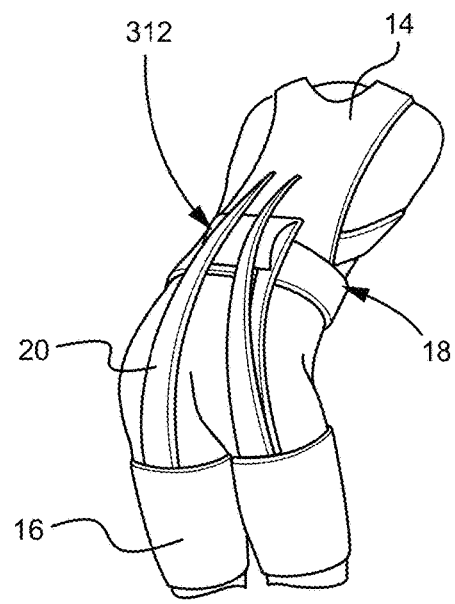

FIGS. 15A-15B are schematic diagrams illustrating an exosuit worn by a user and having moment arm extension system 312 of a flexible member design connected to a waistband portion 18 of the exosuit, in a collapsed configuration and extended configuration, respectively.

With respect to FIGS. 15A-15B, flexible member 322 (comprising, for example, a piece/sheet spring steel of approximately 0.5 to 2 mm thickness, or other flexible material that can return to its original shape after buckling/deforming/bulging when a force applied thereon is lessened or no longer applied) is anchored on the low-back with the use of a back-belt, waistband, or similar device 18. One or more elastic members 20 are attached from the trunk harness 14 to the thigh sleeves 16 (i.e., the trunk-thigh elastic members) and runs directly over the sheet of spring steel. Guides may be employed to prevent the elastic members from sliding off of the spring steel). Other elastic member(s) (i.e., the thigh-only elastic members) attach from the thigh sleeves to the top portion of the spring steel (e.g., at the top edge or closer to the top edge than the bottom edge, of the spring steel). The bottom of the spring steel is anchored to the waist with a waistband. As the user leans forward, all the elastic members are stretched. In particular, the thigh-only elastic members pull down on the spring steel causing it to buckle/deform such that it bulges away from the back. And the trunk-thigh elastic members are pushed away from the body via the extended/buckled spring steel, thereby extending/increasing the moment arm of the exosuit.

The embodiment shown in FIGS. 13A-13B differs from FIGS. 15A-15B in that the moment arm extension system in FIGS. 13A-13B is coupled to the exosuit harness instead of the back-belt, waistband, or similar device in FIGS. 15A-15B.

Figure 16A:
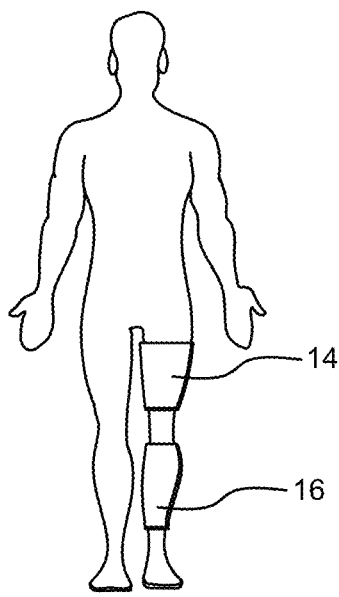
FIGS. 16A-16C are schematic diagrams illustrating an exosuit comprising an upper body interface and a lower body interface worn by a user at alternative locations to assist other body segments. For simplicity purposes, the moment arm extension system (which could be any of the above designs or another design) is not shown. In particular.
Figure 16B:
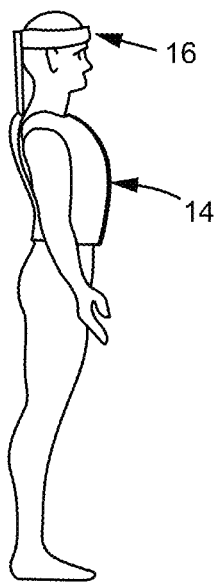
Figure 16C:
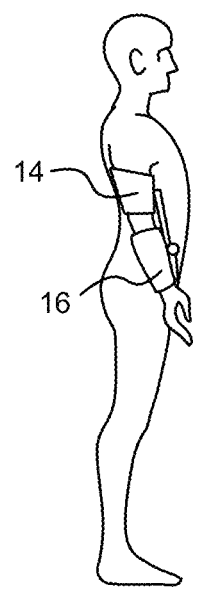

FIGS. 16A-16C are schematic diagrams illustrating an exosuit worn by a user at alternative locations to assist other body segments. For simplicity purposes, the moment arm extension system (which could be any of the above designs or another design) is not shown. In particular, FIG. 16A shows a knee-assist exosuit, FIG. 16B shows a neck-assist exosuit, and FIG. 16C shows a bicep-assist exosuit.

Embodiments described above are directed to an exosuit to be worn on a back of a user, but the same type of moment arm extension systems could alternatively be applied to assist other body segments such as the ankles, knees, hips, elbows, wrists or neck. Example configurations are depicted in FIGS. 16A-16C without the moment arm shown, for simplicity purposes. The upper body and lower body interfaces 14 and 16 do not necessarily have to be located on the trunk and the thigh of a user. Instead, the upper body and lower body interfaces 14 and 16 could both be placed on a single body part, e.g., on the leg above and below the knee (as seen in FIG. 16A) or on bicep and forearm portions of a single arm (as seen in FIG. 16C), with the moment arm extension system between them. In this configuration, the upper body interface 14 would be the bicep interface, and the lower body interface 16 would be the forearm interface. Instead of an exosuit, embodiments of the moment arm extension system could be integrated into clothing items or wearable accessories, such as a baby carrier, bra, vest, or body armor. As seen in FIG. 16B, one body interface 14 may be a vest and the other body interface may be a headband 16.

Various Methods for Controlling the Moment Arm Extension System

The low back exosuit the inventors developed (international publication number WO 2018/136722 by Zelik, et al.)

is a low-profile device that uses a spring (elastic member) in parallel with the wearer's muscles to reduce loading on the lower back. One benefit of this clothing-like assistive suit is that that spring element(s) act at a larger moment arm about the spine than muscles or ligaments. As mentioned above, a larger mechanical advantage could be achieved with a larger moment arm. However, this also makes the device less form-fitting (protruding element from back). One way to achieve the best of both worlds (low profile+more assistance via a larger moment arm) is to have an extendable moment arm that only extends when assistance is provided, but which remains lower profile (closer to body) when not in use. Here we propose a method for achieving that function. There are powered (motorized) and passive (non-motorized) versions of this idea:

The powered version would utilize: (i) body-worn sensors; (ii) portable microprocessor unit; (iii) actuator (with power supply); and (iv) moment arm extension system. The body worn sensors may be wireless and would stream/transmit data back to the microprocessor unit which would log/process the data (note: sensors could also be wired to microprocessor). Examples of sensors would be inertial measurement units or inclinometers placed on the arm segments, pressure insoles worn in shoes, hard-worn load/pressure sensors, or electromyography on the back, trunk or arms. These sensors would monitor the user's movement, for instance the motion of the arms, or load on the arms/hands or under the feet. As task demands increase (e.g., more carried load, or the arms extend out away from the body), the microprocessor (via algorithms) would command the actuator unit to extend the moment arm extension system, increasing the moment arm about the spine. As the task demands decrease, the actuator would be commanded to reduce the moment arm of the moment arm extension system. Examples of powered actuators include electric motors, solenoids, pneumatics and hydraulics. Note that a simple example of using a sensor to control would be just to have a dial on the device/clothes that allowed a person to directly control/vary the extendable member of the moment arm extension system (e.g., change from low profile minimum moment arm to partially or fully extended).

The passive version would involve: (i) moment arm extension system; (ii) cable transmission (optional); and (iii) an interface that anchors the cable to the user. A specific example would involve a Bowden cable that was mounted to the forearm(s) of the wearer. At the other end, the cable would attach to the moment arm extension system. As the user extended their arm(s) away from their body, the extendable member of the moment arm extension system would increase/extend proportionally, and vice versa—as the arms are brought back towards the body, the extendable member would decrease/collapse. Note that this system could take advantage of lever mechanics such that larger motions of the arms would results in smaller motions (extension) of the extendable member. This has the benefit of keeping forces lower at arm (higher displacement) while obtaining higher forces at the extendable member (lower displacement). The arms are given as an example, but other body segments could also be used in the same manner to mechanically control the extendable member. Or even the extendable member could be controlled by a simple mechanical dial that the person turned to affect a desired extendable member length/extension. Various embodiments shown allow the extendable member to be controlled by flexion of the hip or trunk, or other body segments.

Embodiments are directed to a wearable assistance device configured to be worn by a user. The device comprises: an upper body interface; a lower body interface; a moment arm extension system configured to be positioned along a body segment of the user, and be movable between a collapsed configuration and an extended configuration; and one or more elastic members operatively coupling the upper body interface to the lower body interface via the moment arm extension system. The moment arm extension system is operatively connected to at least one of the one or more elastic members at a location between the upper body interface and the lower body interface. The moment arm extension system allows a portion of the at least one of the one or more elastic members to extend away from the body segment when in the extended configuration, and to move towards the body segment when moving from the extended configuration to the collapsed configuration. The portion of the at least one of the one or more elastic members is further from the body segment when in the extended configuration than when in the collapsed configuration, such that the moment arm extension system provides a greater mechanical advantage (e.g., assistive torque or assistive moment of force) by the one or more elastic members about the body segment or another body segment when in the extended configuration than provided by the moment arm extension system when in the collapsed configuration.

In an embodiment, the moment arm extension system comprises: a base configured to be positioned along the body segment; and an extendable member operatively connected to the base. At least a portion of the extendable member extends a greater distance from the base when in the extendable configuration than in the collapsed configuration. The moment arm extension system is operatively connected to the at least one of the one or more elastic members via the extendable member. The moment arm extension system allows a portion of the at least one of the one or more elastic members to extend away from the body segment via the extendable member when in the extended configuration.

In an embodiment, the extendable member is connected to the base via at least one link.

In an embodiment, the at least one of the one or more elastic members is configured to apply a tension force above a threshold (e.g., in the range of 5 to 100 N) on the extendable member such that the moment arm extension system moves from the collapsed configuration to the extended configuration.

In an embodiment, the moment arm extension system further comprises a hinge assembly comprising a rotation axis, and wherein the extendable member is defined by a lever connected to the base via the hinge assembly such that the lever is rotatable about the rotation axis.

In an embodiment, the moment arm extension system is movable between the collapsed configuration and extended configuration via: an actuator; manually by the user; or at least one of the one or more elastic members configured to apply a tension force above a threshold (e.g., in the range of 5 to 100 N) on the lever.

In an embodiment, the device further comprises a lower body elastic member, wherein the moment arm extension system is defined by a flexible member having an upper portion, and wherein the lower body elastic member connects the upper portion to the lower body interface such that when a tension force is applied above a threshold (e.g., in the range of 5 to 100 N) by the lower body elastic member to the upper portion, the moment arm extension system moves from the collapsed configuration to the extended configuration.

In an embodiment, the moment arm extension system moves from the collapsed configuration to the extended configuration via a powered actuation system.

In an embodiment, the body segment is a back of the user.

Embodiments are also directed to a moment arm extension system configured to be worn by a user. The system comprises: a base configured to be positioned along a body segment of the user; and an extendable member operatively connected to the base. The moment arm extension system is movable between a collapsed configuration and an extended configuration. At least a portion of the extendable member extends a greater distance from the base when in the extendable configuration than in the collapsed configuration. The moment arm extension system is configured to operatively connect to at least one elastic member via the extendable member. The moment arm extension system allows a portion of the at least one elastic member to extend away from the body segment via the extendable member when in the extended configuration, and to move towards the body segment when moving from the extended configuration to the collapsed configuration. The portion of the at least one elastic member is further from the body segment when in the extended configuration than when in the collapsed configuration, such that the moment arm extension system provides a greater mechanical advantage by the at least one elastic member about the body segment or another body segment when in the extended configuration than provided by the moment arm extension system when in the collapsed configuration.

In an embodiment, the extendable member is connected to the base via at least one link.

In an embodiment, the at least one elastic member is configured to apply a tension force above a threshold on the extendable member such that the moment arm extension system moves from the collapsed configuration to the extended configuration.

In an embodiment, the moment arm extension system further comprises a hinge assembly comprising a rotation axis, and wherein the extendable member is defined by a lever connected to the base via the hinge assembly such that the lever is rotatable about the rotation axis.

In an embodiment, the at least one elastic member is configured to apply a tension force above a threshold on the lever such that the moment arm extension system moves from the collapsed configuration to the extended configuration.

In an embodiment, the moment arm extension system moves from the collapsed configuration to the extended configuration via a powered actuation system.

In an embodiment, the body segment is a back of the user.

Embodiments are further directed to a moment arm extension system configured to be worn by a user. The system comprises: a flexible member having an upper portion and configured to be positioned along a body segment of the user. The flexible member is movable between a collapsed configuration and an extended configuration. A portion of the flexible member extends a greater distance from the body segment when in the extendable configuration than in the collapsed configuration. The flexible member is configured to allow a portion of an elastic member to extend away from the body segment via the portion of the flexible member when in the extended configuration, and to move towards the body segment when moving from the extended configuration to the collapsed configuration. The portion of the elastic member is further from the body segment when in the extended configuration than when in the collapsed configuration, such that the flexible member provides a greater mechanical advantage by the elastic member about the body segment or another body segment when in the extended configuration than provided by the flexible member when in the collapsed configuration.

In an embodiment, the upper portion is configured to operatively connect to another elastic member such that when a tension force is applied above a threshold by the another elastic member to the upper portion, the flexible member moves from the collapsed configuration to the extended configuration.

In an embodiment, the flexible member moves from the collapsed configuration to the extended configuration via a powered actuation system.

In an embodiment, the body segment is a back of the user.

Embodiments are yet further directed to a method of using a wearable assistance device. The method comprises providing a wearable assistance device to be worn by a user. The wearable assistance device comprises: an upper body interface; a lower body interface; a moment arm extension system positioned along a body segment of the user, and movable between a collapsed configuration and an extended configuration; and one or more elastic members operatively coupling the upper body interface to the lower body interface via the moment arm extension system, wherein the moment arm extension system is operatively connected to at least one of the one or more elastic members at a location between the upper body interface and the lower body interface. The method also comprises extending, via the moment arm extension system, a portion of the at least one of the one or more elastic members away from the body segment when in the extended configuration. The method further comprises moving, via the moment arm extension system, the portion of the at least one of the one or more elastic members towards the body segment when moving from the extended configuration to the collapsed configuration. The portion of the at least one of the one or more elastic members is further from the body segment when in the extended configuration than when in the collapsed configuration, such that the moment arm extension system provides a greater mechanical advantage by the one or more elastic members about the body segment or another body segment when in the extended configuration than provided by the moment arm extension system when in the collapsed configuration.

In any of the above embodiments:
  the extension and collapse of the moment arm extension system may be controlled passively by flexion or extension of one or more body segments.
  the extension and collapse of the moment arm extension system may be controlled actively by an actuator (e.g., motor, solenoid) and sensors (examples of embodiments: voice control, button press, muscle activity sensors). The actuator may apply a force perpendicular to one or more elastic members, or apply a tensile force along one or more elastic members.
  extension of the moment arm extension system may be controlled based on the position or orientation of the trunk, arm, or hand, or other body segment, and which can be implemented using worn sensors, a processor and actuator (e.g., motor), or implemented using a passive transmission system such as a Bowden cable coupling motion of the arms or hands to extension of the extendable member of the moment arm.
  The moment arm extension system may be used within a passive (e.g., elastic) exosuit.
  The moment arm extension system may be used within a quasi-passive or mode-switching (e.g., clutchable spring) exosuit. In this embodiment, the moment arm would remain in collapsed configuration when the clutch was disengaged. When switched into engaged mode, the moment arm would then either extend, or be configured such that it was able to extend based on user movement.

The moment arm extension system may be used within a powered exosuit. A powered exosuit could use a motor with gear or transmission system to directly or indirectly power extension of the moment arm, or to directly or indirectly apply tensile force along an elastic member.

one or more moment arm extension systems may be located on or anchored against the thighs, buttocks, pelvis or back or other body segment.

the motion of the moment arm extension system, or a cam-like shape of its extendable arm, could be employed to provide non-linear torque behavior, and thus enable an exosuit or other wearable assistance device to provide a customized assistive torque profile.

Although embodiments are described above with reference to a moment arm extension system that goes from a collapsed configuration (with no assistance force applied to a body segment) to an extended configuration (with mechanical advantage provided about the body segment), the moment arm extension system described in any of the above embodiments may alternatively have the collapsed configuration providing some amount of mechanical advantage about a body segment while still being less than the amount of mechanical advantage provided about the body segment when in the extended configuration. Such alternatives are considered to be within the spirit and scope of the present invention, and may therefore utilize the advantages of the configurations and embodiments described above.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A wearable assistance device configured to be worn by a user, the device comprising:
   an upper body interface;
   a lower body interface;
   a moment arm extension system configured to be positioned along a body segment of the user, and be movable between a collapsed configuration and an extended configuration; and
   one or more elastic members operatively coupling the upper body interface to the lower body interface via the moment arm extension system;
   wherein the moment arm extension system is operatively connected to at least one of the one or more elastic members at a location between the upper body interface and the lower body interface; and
   wherein the moment arm extension system allows a portion of the at least one of the one or more elastic members to extend away from the body segment when in the extended configuration, and to move towards the body segment when moving from the extended configuration to the collapsed configuration, and wherein the portion of the at least one of the one or more elastic members is further from the body segment when in the extended configuration than when in the collapsed configuration, such that the moment arm extension system provides a greater mechanical advantage by the one or more elastic members about the body segment or another body segment when in the extended configuration than provided by the moment arm extension system when in the collapsed configuration; wherein the moment arm extension system comprises: a base configured to be positioned along the body segment; and an extendable member operatively connected to the base; wherein at least a portion of the extendable member extends a greater distance from the base when in the extendable configuration than in the collapsed configuration; wherein the moment arm extension system is operatively connected to the at least one of the one or more elastic members via the extendable member; and wherein the moment arm extension system allows a portion of the at least one of the one or more elastic members to extend away from the body segment via the extendable member when in the extended configuration; wherein the moment arm extension system further comprises a hinge assembly comprising a rotation axis, and wherein the extendable member is defined by a lever connected to the base via the hinge assembly such that the lever is rotatable about the rotation axis.

2. The wearable assistance device of claim 1, wherein the extendable member is connected to the base via at least one link.

3. The wearable assistance device of claim 1, wherein the at least one of the one or more elastic members is configured to apply a tension force above a threshold on the extendable member such that the moment arm extension system moves from the collapsed configuration to the extended configuration.

4. The wearable assistance device of claim 1, wherein the moment arm extension system is movable between the collapsed configuration and extended configuration via: an actuator; manually by the user; or at least one of the one or more elastic members configured to apply a tension force above a threshold on the lever.

5. The wearable assistance device of claim 1, wherein the device further comprises a lower body elastic member, wherein the moment arm extension system is defined by a flexible member having an upper portion, and wherein the lower body elastic member connects the upper portion to the lower body interface such that when a tension force is applied above a threshold by the lower body elastic member to the upper portion, the moment arm extension system moves from the collapsed configuration to the extended configuration.

6. The wearable assistance device of claim 1, wherein the moment arm extension system moves from the collapsed configuration to the extended configuration via a powered actuation system.

7. The wearable assistance device of claim 1, wherein the body segment is a back of the user.

8. A moment arm extension system configured to be worn by a user, the system comprising:
  a base configured to be positioned along a body segment of the user; and
  an extendable member operatively connected to the base;
  wherein the moment arm extension system is movable between a collapsed configuration and an extended configuration, and wherein at least a portion of the extendable member extends a greater distance from the base when in the extendable configuration than in the collapsed configuration;
  wherein the moment arm extension system is configured to operatively connect to at least one elastic member via the extendable member; and
  wherein the moment arm extension system allows a portion of the at least one elastic member to extend away from the body segment via the extendable member when in the extended configuration, and to move towards the body segment when moving from the extended configuration to the collapsed configuration, and wherein the portion of the at least one elastic member is further from the body segment when in the extended configuration than when in the collapsed configuration, such that the moment arm extension system provides a greater mechanical advantage by the at least one elastic member about the body segment or another body segment when in the extended configuration than provided by the moment arm extension system when in the collapsed configuration; wherein the moment arm extension system further comprises a hinge assembly comprising a rotation axis, and wherein the extendable member is defined by a lever connected to the base via the hinge assembly such that the lever is rotatable about the rotation axis.

9. The moment arm extension system of claim 8, wherein the extendable member is connected to the base via at least one link.

10. The moment arm extension system of claim 8, wherein the at least one elastic member is configured to apply a tension force above a threshold on the extendable member such that the moment arm extension system moves from the collapsed configuration to the extended configuration.

11. The moment arm extension system of claim 8, wherein the at least one elastic member is configured to apply a tension force above a threshold on the lever such that the moment arm extension system moves from the collapsed configuration to the extended configuration.

12. The moment arm extension system of claim 8, wherein the moment arm extension system moves from the collapsed configuration to the extended configuration via a powered actuation system.

13. The moment arm extension system of claim 8, wherein the body segment is a back of the user.

14. A moment arm extension system configured to be worn by a user, the system comprising:
  a flexible member having an upper portion and configured to be positioned along a body segment of the user;
  wherein the flexible member is movable between a collapsed configuration and an extended configuration, and wherein a portion of the flexible member extends a greater distance from the body segment when in the extendable configuration than in the collapsed configuration; and
  wherein the flexible member is configured to allow a portion of an elastic member to extend away from the body segment via the portion of the flexible member when in the extended configuration, and to move towards the body segment when moving from the extended configuration to the collapsed configuration, and wherein the portion of the elastic member is further from the body segment when in the extended configuration than when in the collapsed configuration, such that the flexible member provides a greater mechanical advantage by the elastic member about the body segment or another body segment when in the extended configuration than provided by the flexible member when in the collapsed configuration; wherein the flexible member comprises thin spring steel.

15. The moment arm extension system of claim 14, wherein the upper portion is configured to operatively connect to another elastic member such that when a tension force is applied above a threshold by the another elastic member to the upper portion, the flexible member moves from the collapsed configuration to the extended configuration.

16. The moment arm extension system of claim 14, wherein the flexible member moves from the collapsed configuration to the extended configuration via a powered actuation system.

17. The moment arm extension system of claim 14, wherein the body segment is a back of the user.

18. A method of using a wearable assistance device, the method comprising:
  providing a wearable assistance device to be worn by a user, the wearable assistance device comprising:
    an upper body interface;
    a lower body interface;
    a moment arm extension system positioned along a body segment of the user, and movable between a collapsed configuration and an extended configuration; and
    one or more elastic members operatively coupling the upper body interface to the lower body interface via the moment arm extension system, wherein the moment arm extension system is operatively connected to at least one of the one or more elastic members at a location between the upper body interface and the lower body interface;
  extending, via the moment arm extension system, a portion of the at least one of the one or more elastic members away from the body segment when in the extended configuration; and
  moving, via the moment arm extension system, the portion of the at least one of the one or more elastic members towards the body segment when moving from the extended configuration to the collapsed configuration;
  wherein the portion of the at least one of the one or more elastic members is further from the body segment when in the extended configuration than when in the collapsed configuration, such that the moment arm extension system provides a greater mechanical advantage by the one or more elastic members about the body segment or another body segment when in the extended configuration than provided by the moment arm extension system when in the collapsed configuration; wherein the moment arm extension system comprises: a base configured to be positioned along the body segment; and an extendable member operatively connected to the base; wherein at least a portion of the extendable member extends a greater distance from the base when in the extendable configuration than in the collapsed configuration; wherein the moment arm extension system is operatively connected to the at least one of the one or more elastic members via the extendable member; and wherein the moment arm extension system allows a portion of the at least one of the one or more elastic members to extend away from the body segment via the extendable member when in the extended configuration; wherein the moment arm extension system further comprises a hinge assembly comprising a rotation axis, and wherein the extendable member is defined by a lever connected to the base via the hinge assembly such that the lever is rotatable about the rotation axis.

* * * * *